(12) United States Patent
Day et al.

(10) Patent No.: US 10,238,772 B2
(45) Date of Patent: Mar. 26, 2019

(54) BIODEGRADABLE COMPOSITE SCAFFOLD FOR REPAIRING DEFECTS IN LOAD-BEARING BONES

(71) Applicants: Delbert E. Day, Rolla, MO (US); Ali Mohammadkhah, Rolla, MO (US)

(72) Inventors: Delbert E. Day, Rolla, MO (US); Ali Mohammadkhah, Rolla, MO (US)

(73) Assignee: The Curators of the University of Missouri, Columbia, MO (US)

(*) Notice: Subject to any disclaimer, the term of this patent is extended or adjusted under 35 U.S.C. 154(b) by 1285 days.

(21) Appl. No.: 14/216,451

(22) Filed: Mar. 17, 2014

(65) Prior Publication Data

US 2014/0277578 A1 Sep. 18, 2014

Related U.S. Application Data

(60) Provisional application No. 61/786,950, filed on Mar. 15, 2013.

(51) Int. Cl.
| | |
|---|---|
| *A61L 27/42* | (2006.01) |
| *A61L 27/34* | (2006.01) |
| *A61L 27/44* | (2006.01) |
| *A61L 27/56* | (2006.01) |
| *A61L 27/58* | (2006.01) |

(52) U.S. Cl.
CPC .............. *A61L 27/427* (2013.01); *A61L 27/34* (2013.01); *A61L 27/446* (2013.01); *A61L 27/56* (2013.01); *A61L 27/58* (2013.01); *A61L 2430/02* (2013.01)

(58) Field of Classification Search
CPC .... A61L 27/427; A61L 27/56; A61L 2430/02; A61L 27/34; A61L 27/58; A61L 27/446
See application file for complete search history.

(56) References Cited

U.S. PATENT DOCUMENTS

| | | | |
|---|---|---|---|
| 5,013,323 A * | 5/1991 | Kobayashi | A61L 27/46 501/1 |
| 6,993,406 B1 | 1/2006 | Cesarano, III et al. | |
| 8,173,154 B2 | 5/2012 | Jung et al. | |
| 8,287,896 B2 | 10/2012 | Jung et al. | |
| 8,337,875 B2 | 12/2012 | Jung et al. | |
| 8,353,966 B2 | 1/2013 | Day et al. | |
| 8,481,066 B2 | 7/2013 | Day et al. | |
| 8,551,513 B1 | 10/2013 | Jung et al. | |
| 2002/0160175 A1 | 10/2002 | Pirhonen | |
| 2004/0267362 A1 | 12/2004 | Hwang et al. | |
| 2007/0255422 A1* | 11/2007 | Wei | A61F 2/28 623/23.51 |
| 2010/0121463 A1* | 5/2010 | Tormala | A61L 27/446 623/23.75 |
| 2010/0179667 A1* | 7/2010 | Day | A61L 27/10 623/23.72 |
| 2011/0014261 A1* | 1/2011 | Day | A61L 27/10 424/423 |
| 2011/0165217 A1 | 7/2011 | Jung et al. | |

(Continued)

*Primary Examiner* — Phong Son H Dang

(74) *Attorney, Agent, or Firm* — Stinson Leonard Street LLP

(57) ABSTRACT

A tissue scaffold for repair and regeneration of bone hard tissue or muscle, skin, or organ soft tissue, including load-bearing bone tissue, the scaffold comprising a core of biocompatible, biodegradable inorganic glass fibers; and a biocompatible, biodegradable, flexible polymer film surrounding the core and adhered to the core.

32 Claims, 20 Drawing Sheets

(56) References Cited

U.S. PATENT DOCUMENTS

2012/0276218 A1   11/2012  Jung et al.
2013/0144400 A1    6/2013  Day et al.
2014/0271786 A1*  9/2014  Bagga .................... A61L 27/56
                                                                     424/443

* cited by examiner

BIODEGRADABLE COMPOSITE SCAFFOLD FOR REPAIRING DEFECTS IN LOAD-BEARING BONES

REFERENCE TO RELATED APPLICATION

This application claims priority to provisional application 61/786,950 filed Mar. 15, 2013, the entire disclosure of which is incorporated by reference.

FIELD OF THE INVENTION

This invention relates to a biodegradable, composite scaffold for repairing load-bearing bones (cortical bone) in humans.

BACKGROUND

Bioactive silicate glasses have found application for forming scaffolds for repairing human tissue. These glasses are advantageous in such applications in view of their biodegradability, biocompatibility, and ability to form a chemically strong bond to living bone.

But because of the inherent brittleness and low tensile strength of bioactive silicate glasses, such as the well known 45S5 glass, the commercial use of bioactive glasses is currently limited to non-load bearing bone sites. A main reason why bioactive glasses are not being used to repair load-bearing bones is their low mechanical strength and brittle failure characteristics, particularly when subjected to tensile and flexural (bending) stresses. While glass has a high compressive strength, it is much weaker when subjected to tensile/bending stresses. The loading conditions that a bioactive glass scaffold might encounter at a load-bearing bone site (e.g., the repair of a broken femur in the leg) can be quite variable, ranging from compressive stresses to tensile and bending stresses. Glass being a brittle material may fail catastrophically under such conditions and this limits its use in the body where it might be subjected to tensile/bending stresses.

SUMMARY OF THE INVENTION

Briefly, therefore, the invention is directed to a tissue scaffold for repair and regeneration of bone hard tissue or muscle, skin, or organ soft tissue, including load-bearing bone tissue, the scaffold comprising a core of biocompatible, biodegradable inorganic glass fibers; and a biocompatible, biodegradable, flexible polymer film surrounding the core and adhered to the core; and wherein the flexural strength of the composite scaffold is at least about 40 MPa.

DETAILED DESCRIPTION OF PREFERRED EMBODIMENTS

The current invention is based on the inventors' discovery that a composite scaffold composed of a biodegradable polymer surrounding a core of generally co-aligned, biodegradable glass fibers is a way to achieve the flexural strength needed for load bearing bone applications.

The invention involves first preparing a scaffold body core. A polymer film is then wrapped around the scaffold body core of longitudinally co-aligned fibers. The polymer film is then adhered to the core by, for example, heating the film. The polymer may have heat-shrink characteristics to squeeze the fiber core. Alternative ways to apply the film are to spray a liquid polymer film (layer) on the surface of the scaffold body core, to "paint" a polymer film (layer) on the surface of the scaffold body core, or to dip the core into a liquid polymer followed by hardening.

The tissue scaffold of the present invention is prepared from fibers which are preferably aligned so that a majority of the fibers are substantially aligned in a parallel direction. The scaffold is prepared by placing and orienting fibers in a unidirectional manner in a mold. The fibers in the mold are heated to a temperature where the fibers soften and bond together. In one preferred embodiment, the fibers are self-bonded in the sense that no adhesive, braze, or other external bonding agent is used for bonding. An alternative embodiment employs a biocompatible agent or adhesive to facilitate bonding, such that the fibers are not self-bonded, at least in part. Upon cooling, the assemblage of bonded fibers is sufficiently rigid and strong that the assemblage can be removed from the mold and handled.

The orientation of the fibers in a lengthwise direction in the self-bonded scaffold provides lengthwise channels (or connected pores) among the fibers, which channels provide for uptake into the scaffold of stem cells, growth factors, medicines, red blood cells and other bodily fluids and components carried in bodily fluids. The fibers are arranged to define channels within the scaffold which facilitate fluid flow into and lengthwise within the scaffold from one end to the other end. The orientation also provides for channels in a transverse direction generally perpendicular to the lengthwise direction of the oriented fibers, to facilitate uptake of fluids from the outer surface of the interior or core of the scaffold. These longitudinal and transverse channels exert significant capillary forces on a liquid which cause the liquid to be drawn into the scaffold. This capillary action facilitates the distribution of these fluids and components relatively uniformly through the scaffold and enables fluids to flow from one end of the scaffold to the other or to enter the scaffold from its surface and transmit the liquid to its ends.

Figure 1A:
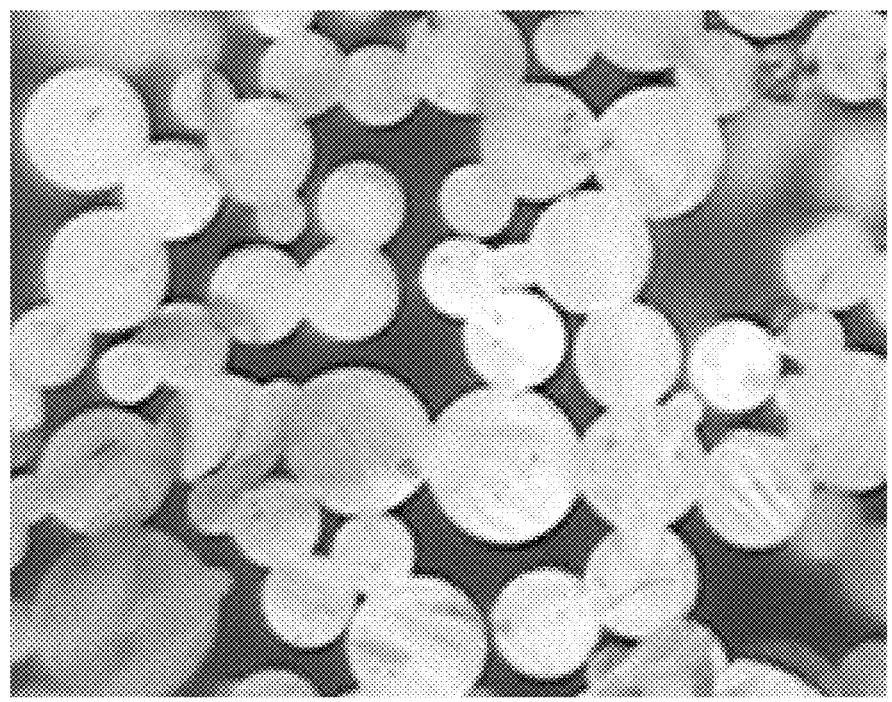
FIG. 1A is an optical micrograph of a transverse cross section of a scaffold core of the invention formed by heating fibers at 700° C. for a relatively shorter time than with the scaffold core in FIGS. 1B and 1C.
Figure 1B:
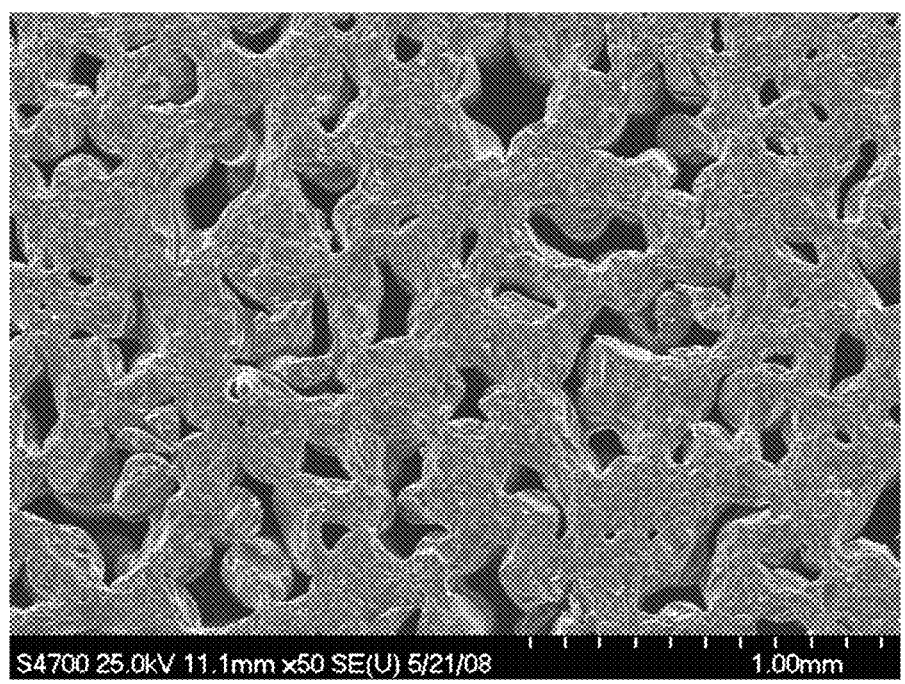
FIGS. 1B and 1C are SEM photographs of a transverse cross section of a scaffold core of the invention formed by heating fibers at 700° C. for a relatively longer time than with the scaffold in FIG. 1A.
Figure 1C:
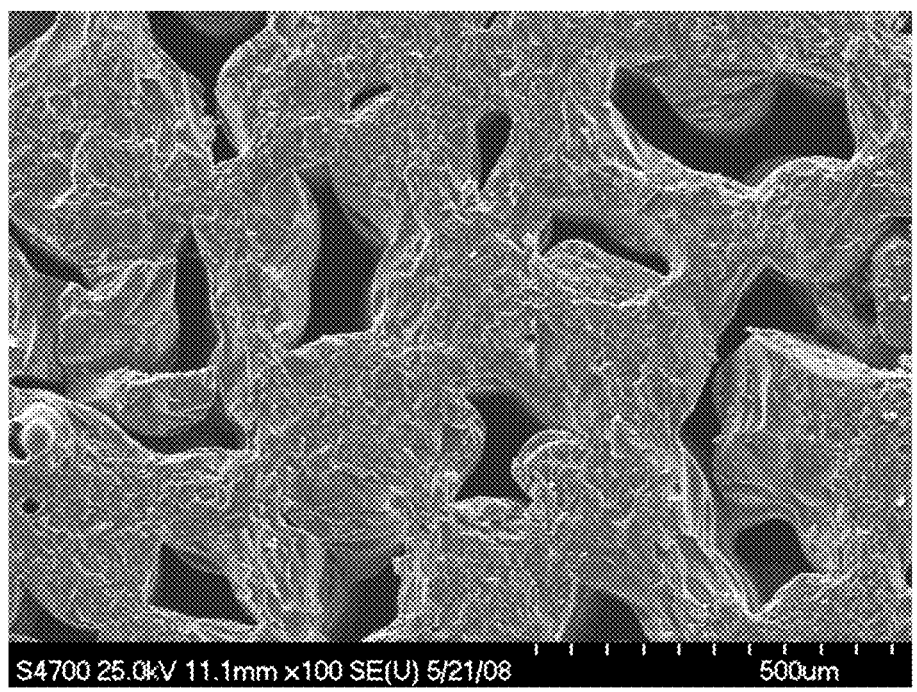

The invention in one embodiment employs fibers having a diameter, prior to molding and softening, between about 20 and about 5000 microns, such as between about 50 and about 5000 microns. In one embodiment the scaffold is prepared from fibers having diameters between about 100 and about 450 microns, such as between about 100 and about 300 microns. In an alternative embodiment, the scaffold is prepared from fibers having diameters up to about 3000 or 5000 microns (3 to 5 mm), which can be deemed more akin to rods than fibers in some contexts, but for purposes of the discussion of this invention fall within the definition of "fibers." FIG. 1A is an optical micrograph of a cross section of a scaffold of the invention showing the self-bonded fibers and pores after heating the fibers at 700° C. for 15 minutes. FIGS. 1B and 1C, which are SEM photographs of a transverse cross section of a different scaffold of the invention having undergone a greater degree of softening and bonding than the scaffold of FIG. 1A, show that after molding and joining to a greater degree (heating at 700° C. for 45 minutes), the transverse cross section of each fiber is no longer precisely circular as it is in a freshly formed fiber. Rather, the softening of the fibers and fusing of adjacent fibers to each other imparts an irregular and irregularly rounded shape to the fibers in transverse cross section. The transverse cross sections here reflect joined fiber cross sections ranging in width—loosely, diameter—from about 50 to about 300 microns.

Figure 2:
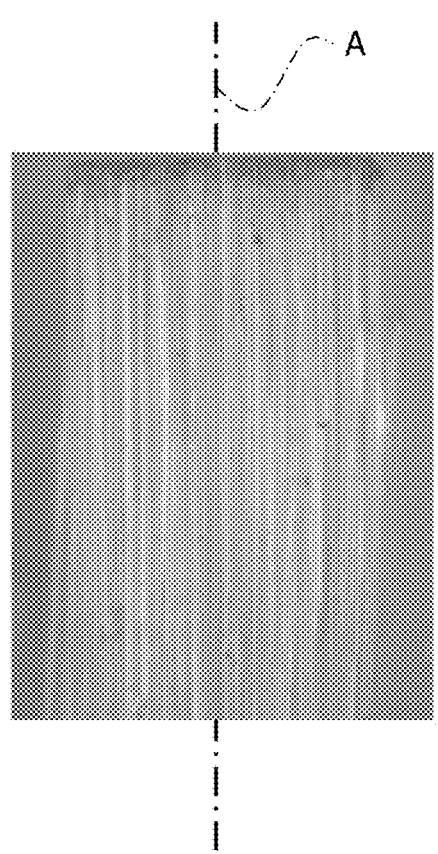
FIG. 2 is a photograph of a lengthwise cross section of a scaffold core of the invention showing lengthwise and parallel alignment of fibers.

The fibers in the scaffold are preferably bonded together and therefore are not loose fibers; but they retain their identities as separate fibers as shown in FIG. 2, which is a photograph of a longitudinal cross section of a scaffold (heated at 700° C.) of the invention. In one aspect of the invention, at least about 75 or 85% by volume of the fibers in the scaffold are longitudinally co-aligned. In this regard the fibers are co-aligned longitudinally, where "co-aligned longitudinally" and the like phrases (e.g., "in lengthwise co-alignment") as applied to a group of adjacent, bundled, or joined fibers in this application means that the alignment of each fiber in the group at any one place along at least about 75% of its length does not deviate more than about 25 degrees from parallel to the central axis of the scaffold. In one preferred embodiment, each fiber in the group at any one place along at least about 75% of its length does not deviate more than about 15 degrees from parallel to the central axis of the scaffold. In another preferred embodiment, each fiber in the group at any one place along at least about 75% of its length does not deviate more than about 10 degrees from the central axis of the scaffold. So it is evident that this co-alignment aspect does not require 100% precise co-alignment of all fibers. The longitudinal co-alignment aspect also allows for some minor deviation of specific segments of individual fibers to an orientation outside these 25, 15, and 10 degree requirements. This is reflected in the requirement that the longitudinal co-alignment is of each fiber along at least 75% of its length, rather than necessarily along its entire length. So up to about 25% of the length of an individual fiber may be misaligned because, for example, it was bent during the scaffold-making process or otherwise. It can be seen therefore in FIG. 2 that each fiber in the scaffold is not absolutely straight, nor is it lying along an absolutely straight line strictly parallel to all other fibers in the scaffold. And each fiber is oriented generally in the same direction, but each is not oriented in exactly the same direction. Moreover, the scaffold itself in certain embodiments is curved, bent, or otherwise not straight, in which cases the central axis of the scaffold to which the alignment of the fibers is within 25 degrees of parallel is also curved, bent, or otherwise not straight. It will also be evident that in certain embodiments a straight or curved scaffold will be machined into a more complex shape as in below Example 6, in which instance the scaffold central axis refers to the central axis as molded and prior to machining.

In order to allow capillary action and channel-forming, the scaffold theoretically contains at least three fibers, although from FIG. 2 it can be seen that the scaffold typically comprises dozens and even hundreds of fibers. It can also be seen that the fibers lie generally lengthwise of the scaffold central axis A (i.e., lie generally in the direction of the central axis) and are generally free of helical orientation about the scaffold central axis. This arrangement applies to at least about 75 vol % of the fibers and preferably to substantially all of the fibers. The fibers shown here extend generally parallel to the scaffold central axis A, which is also illustrated as axis B in FIG. 3C, and axis C in below Example 6. This embodiment also manifests an optional feature that at least about 75 vol % of the fibers occupies the entire length of the scaffold; but in other embodiments this is not the case.

The requirement of the invention that the fibers are co-aligned longitudinally contemplates that the fibers are positioned so that they have a similar alignment, which similar alignment may be straight, bent, or curved. In a separate and distinct aspect of certain preferred embodiments, this common alignment is limited to a generally straight alignment along at least about 75%, 85%, or 95% of the length of the fibers. In other words, at least about 75%, 85%, or 95% of each fiber is generally straight, i.e., at least about 75%, 85%, or 95% of the length of each fiber has an alignment which is within 10 degrees of a mean straight central axis for the fiber. So up to 5%, 15%, or 25% of the length of each fiber may be curved, bent, or otherwise deviate more than 10 degrees from straight in relation to the overall fiber length, but the rest of each fiber is generally straight in that it so deviates less than 10 degrees. In one preferred embodiment, substantially the entire length of each fiber is generally straight in that it deviates less than 10 degrees from the fiber's average central axis. The "mean straight central axis" is the imaginary central axis for the fiber which is absolutely straight and is an average of all axes along the fiber length.

The fibers in the scaffold are selected to have characteristics suitable for the specific application. In one embodiment, the fibers have a length between about 6 mm and about 15 cm, such as between about 12 mm and about 10 cm or between about 25 mm and about 75 mm. Each fiber has a length which is at least about 10 times its diameter. "Diameter" as used herein refers to the fibers largest dimension transverse to its length, and it does not imply that the fibers are perfectly circular in cross section. Each fiber therefore has a fiber lengthwise dimension which is at least about 10 times the fiber transverse dimension, e.g., diameter. In one embodiment, the fiber length is selected so that all, substantially all, or at least about 85 vol % of the individual fibers extend the entire length of the scaffold. The fibers may be selected to have a pre-molding, pre-joining length which corresponds to the length of the scaffold. Or in most embodiments, the length of the fibers is longer than the desired ultimate scaffold length, and the scaffold is cut to the desired length after molding and joining. In an alternative embodiment, the length of a substantial portion (e.g., at least 40 vol %) or all of the fibers is significantly less than the entire length of the scaffold.

FIGS. 1A, 1B, 1C and the below Example 3 also demonstrate the open and interconnected porosity of the scaffold of the invention. The scaffold is manufactured to have a sufficiently high open and interconnected porosity from end to end of the scaffold to facilitate capillary flow of fluids such as bodily fluids and medicines and components they carry through the length of the scaffold, as well as generally transverse from outside walls of the scaffold into the scaffold interior in directions generally transverse to the longitudinal dimension of the fibers. And the scaffold is manufactured so that the ultimate porosity is low enough that the scaffold has required strength for handling, implantation, and service after implantation. If the porosity is too high, the scaffold risks breakage in service, depending on where it is implanted and the loads it encounters. In a preferred embodiment, the porosity as measured in volume is between about 10% and about 35%, for example between about 10% and about 30%, or between about 10% and about 25%. The porosity is controllable mainly by controlling the degree of softening of the fibers, in that highly softened fibers fuse together more completely to a structure with lower porosity. The degree of softening and fusing is controlled by controlling the joining temperature and time. Porosity is also affected by the fiber diameter and by the range in fiber diameter within a given scaffold. Porosity tends to increase with an increasing range in fiber diameter.

The scaffold of the invention in certain preferred embodiments for use in bone repair has a compressive strength between about 20 and about 250 MPa, for example between about 20 and about 180 MPa or between about 80 and about 140 MPa.

The fibers used in many embodiments of the invention are glass where glass is defined as being at least 99 wt % an amorphous or non-crystalline solid, for example made by fusing a mixture of oxides such as $SiO_2$, $B_2O_3$, $P_2O_5$ (known as glass forming oxides) with basic oxides such as the alkali and alkaline earth oxides. In an alternative embodiment, the fibers include glass ceramics fibers that contain both glassy and crystalline regions which in many respects function in the same manner as a fiber that is completely (100%) non-crystalline. It is acceptable in some applications if the glass fiber crystallizes during the bonding step. The fibers may alternatively be pre-reacted bioactive glasses such as glass fibers pre-reacted to have a thin surface layer of hydroxyapatite. These foregoing different types of fibers are within a common group which are referred to herein as "glass fibers." In a further alternative, the unidirectional scaffold comprises crystalline fibers (such as titanium wires) that would also provide a high amount of capillary action. Alternatively, the scaffold comprises a mix of different types of fibers selected from among these.

The fibers are preferably made from a material which is inorganic and which is biocompatible in that the fibers do not have adverse effects when implanted into mammals. Biocompatible materials include both bioactive and bioinert materials. In certain preferred embodiments, the fibers are also of a bioactive glass in that they are of a glass material which reacts with phosphorus such as phosphorus in bodily fluids to form hydroxyapatite. Bioactive glasses are known in the art, for example, from U.S. Pat. No. 6,054,400. Bioactive glasses are available, for example, from Mo-Sci Corporation of Rolla, Mo. In other embodiments, some or all of the fibers may be bioinert rather than bioactive, such as 100% bioinert fibers or a roughly 50/50 mix of bioinert and bioactive fibers.

In general, bioactive glass is one which contains calcium and, when placed in contact with natural body fluids or simulated body fluids, forms a biocompatible calcium phosphate compound such as hydroxyapatite. When such a glass is immersed in or otherwise contacted with natural or simulated body fluids which contain phosphate ions such as in a mammal, the glass dissolves, thereby releasing $Ca^{2+}$ ions into the solution. In this solution, $Ca^{2+}$ ions react with $PO_4^{3-}$ and $OH^-$ ions to form a calcium phosphate which has a relatively low solubility limit in the aqueous phosphate solution. As the dissolution of the glass proceeds, the concentration of calcium phosphate increases in the solution until the solubility limit of calcium phosphate is exceeded and, as a consequence, hydroxyapatite (a form of calcium phosphate) is deposited as a porous layer on the outer surface of the dissolving glass. The formation of this porous hydroxyapatite layer on the glass surface, however, does not prevent further dissolution of the glass. Rather, the glass continues to dissolve and, as it does, the thickness of the porous hydroxyapatite layer increases. Eventually, the glass is completely reacted or transformed, leaving only a porous hydroxyapatite substance whose shape and size are the same as the initial glass fiber. Hydroxyapatite has crystallographic and chemical properties similar to those of mammalian bone. For example, human bone is a composite of fibrous protein, collagen, and hydroxyapatite.

The material for use in the invention is also selected to be of a composition which is available in fibers or which can be pulled into fibers. Glass fibers can be made several ways. For example, glass fibers can be made by pulling by hand or with use of a rotating drum directly from a melt, or they can be pulled through a bushing of a particular size. The composition is preferably selected to be of a type which softens to facilitate self-joining at a temperature below its crystallization temperature. Suitable bioactive glasses include, for example those listed in Table 1.

TABLE 1

Weight Percent Composition of Bioactive Glasses

| $Li_2O$ | $Na_2O$ | $K_2O$ | MgO | CaO | $B_2O_3$ | $P_2O_5$ | $SiO_2$ |
|---|---|---|---|---|---|---|---|
| 0 | 20 | 10 | 5 | 10 | 0 | 0 | 55 |
| 0 | 18 | 9 | 0 | 14 | 1 | 4 | 54 |
| 0 | 12 | 15 | 5 | 11 | 1 | 2 | 54 |
| 0 | 6 | 12 | 5 | 20 | 0 | 4 | 53 |
| 0 | 18 | 6 | 2 | 17 | 2 | 2 | 53 |
| 0 | 15 | 12 | 2 | 11 | 3 | 4 | 53 |
| 0 | 20 | 10 | 2 | 10 | 3 | 3 | 52 |
| 0 | 20 | 10 | 5 | 10 | 3 | 0 | 52 |
| 0 | 25 | 5 | 2 | 10 | 3 | 3 | 52 |
| 0 | 15 | 15 | 2 | 15 | 3 | 0 | 50 |
| 0 | 6 | 12 | 5 | 20 | 17.7 | 4 | 35.3 |
| 0 | 6 | 12 | 5 | 20 | 35.3 | 4 | 17.7 |
| 0 | 6 | 12 | 5 | 20 | 53 | 4 | 0 |
| 0 | 21.5 | 0 | 0 | 21.5 | 0 | 4 | 53 |
| 11.5 | 0 | 0 | 0 | 10 | 78.5 | 0 | 0 |
| 10.7 | 0 | 0 | 0 | 15 | 74.3 | 0 | 0 |
| 10 | 0 | 0 | 0 | 20 | 70 | 0 | 0 |

Glasses which crystallize under fiber-pulling conditions and/or which crystallize at a temperature below that where they soften sufficiently for joining such as 45S5 have some limited applications here but are generally avoided in the preferred embodiments because they become too brittle and weak. Bioactive glasses such as 45S5 and other glasses that crystallize quickly not allowing sufficient self-bonding to occur may be bonded with sodium silicate or some other bonding agent to form an alternative scaffold embodiment of the invention; however the strength will likely be relatively low in comparison with self-bonded scaffolds.

Figure 3A:
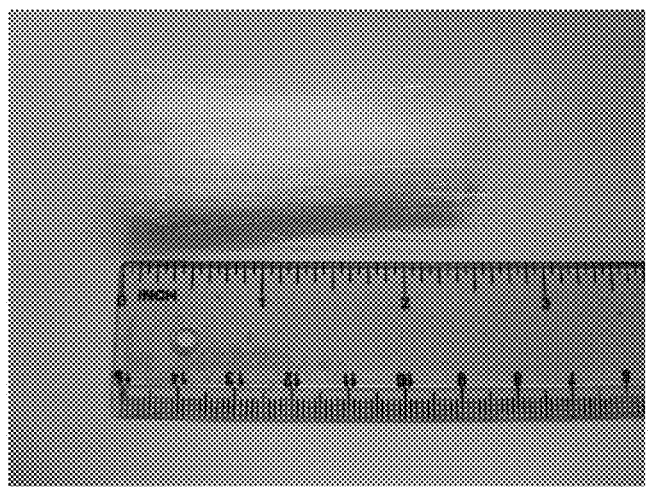
FIGS. 3A, 3B, and 3C are a series of photographs showing the manufacturing progression of a scaffold core from loose fibers to a self-bonded scaffold core for use in the invention.
Figure 3B:

In forming the scaffold core of the invention, a bundle of glass fibers such as the 6.25 cm long loose cut fibers shown in FIG. 3A is placed as shown in 3B in a mold or similar vessel which, upon softening, joining, and cooling of the glass, will impart the desired final shape and strength to the scaffold core. Each of the bundles inserted as shown in FIG. 3B weighs about 2.4 grams and the mold is about 5.6 cm long. In one embodiment, this vessel is a graphite mold such as a hollowed out cylinder as shown in 3B. The fibers are placed in the vessel tightly enough to fill the vessel cavity, but not so tightly as to risk breakage of the fibers or excessive densification. The vessel is then placed in a furnace and heated at a rate of about 20° C./min in the presence of a suitable atmosphere such as air, oxygen, or nitrogen. The temperature and the heating time are selected depending on the glass composition to achieve softening and bonding of the fibers while avoiding too much bonding which would not achieve the desired porosity. The joining is preferably self-joining in that the softening of the glass accomplishes joining and no added joining agents are employed. That is, the scaffold body consists only of joined fiber elements and no other elements. As a general proposition, the vessel is heated to a temperature between about 500 and about 800° C. and held at that temperature for between about 5 and about 60 minutes. For example, in one embodiment where the scaffold is formed from type 13-93 glass fibers to a finished dimension of about 62.5 mm long and about 6 mm in diameter, the vessel is heated to a temperature between about 695 and about 705° C. and held at that temperature for between about 5 and about 45 minutes. After bonding, the vessel and scaffold are cooled, preferably in air, at a rate which avoids cracking of the bonded fibers, such as between about 10 and about 30° C. per minute.

Figure 3C:
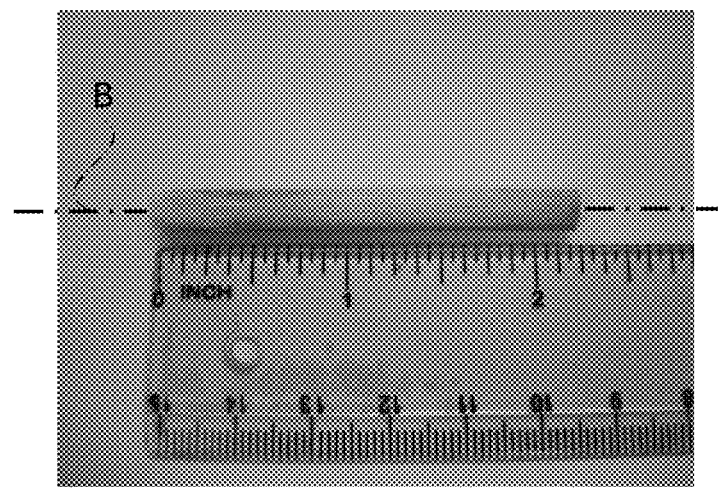

The scaffold is then removed from the vessel and cut to the desired length to yield the product shown in FIG. 3C. Cutting is accomplished, for example, by filling the pores with a wax, cutting the scaffold to length with a sharp, non-burring (e.g., diamond) saw, and then chemically or thermally removing the wax. Sharp corners and edges are avoided by making clean cuts while the scaffold is impregnated with wax, or a polish can be done with either grinding paper or a mechanical polishing device such as a Dremel tool, also done while wax impregnated.

The scaffold can be pre-reacted in a phosphate solution such as simulated body fluid (SBF) or an alkali phosphate solution to form a reacted surface layer of hydroxyapatite, prior to sterilization and implantation in a mammal. The hydroxyapatite surface layer thickness can be controlled by predetermined conversion kinetics of the glass in a phosphate containing solution. Heat treatment of the glass can induce glass crystallization which may be beneficial in the formation of glass-ceramics or ceramics. Chemical (acid) etching may add surface roughness which could be beneficial to cell attachment. Heat treating the glass to cause phase separation to form multiple phases which could react at different rates and form a new microstructure within the individual self-bonded fibers is desirable in certain applications. It is also within the scope of this invention to incorporate additives such as growth factors, medicines, etc. into the scaffold body which perform a function such as assist with tissue regrowth or supplement reinforcement of the body. In most preferred embodiments, such additives or reinforcements constitute less than about 10 vol. % of the scaffold, such that the fibers and the porosity cumulatively constitute at least about 75 vol. % of the scaffold body, for example at least about 90 vol. %. And in some embodiments there are no such additives or reinforcements, such that the scaffold body consists essentially of the fibers and the porosity.

After the wax has been removed, the scaffold cores are sterilized. A preferred method among several possible is dry heat sterilization. The scaffolds are placed in a clean glass vial, covered with a clean aluminum foil cap, and heated to approximately 300° C. for three to four hours. Upon cooling, the sterile scaffolds are ready to be implanted.

Growth factors, medicines such as antibiotics, seeded cells or other biological material, liquids or gels of any type, coatings (particles, spheres, hollow spheres, thin film(s), fibers, and hollow fibers), an interpenetrating phase such as a biodegradable polymer or bone cement (PMMA) or other biological polymer, other organic or inorganic materials, or any combination may be added after sterilization to promote the growth of tissues into the scaffold. Additional sterilization may be required for scaffolds that have had inorganic non-sterile components added, and the method of sterilization may vary with the material(s) added.

In one alternative embodiment of the invention, a titanium or other biocompatible support such as a rod is incorporated into the scaffold to provide additional mechanical strength, as described in some of the working examples.

Figure 4:
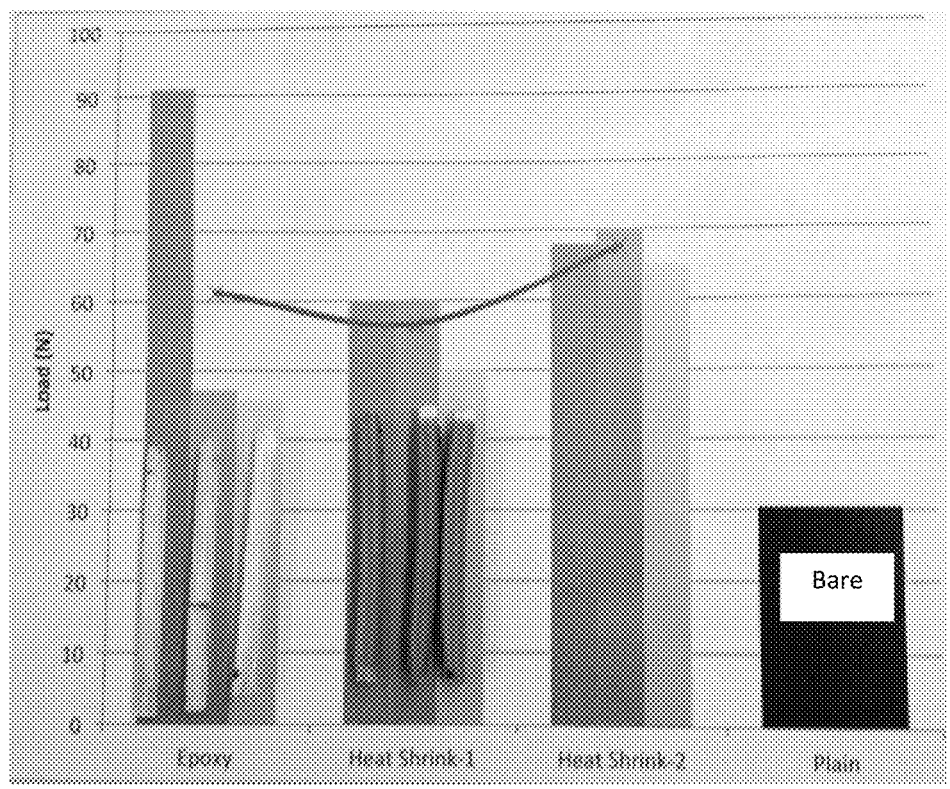
FIG. 4 is a photograph showing two sets of three scaffolds of the invention against a background showing flexural strength data for three sets of scaffolds of the invention and one set of control scaffolds.
Figure 5:
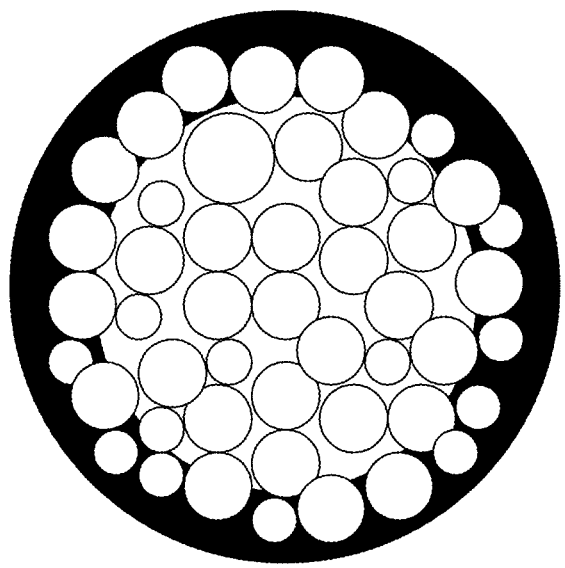
FIG. 5 is a schematic representation of a cross section of a scaffold of the invention.
Figure 6:
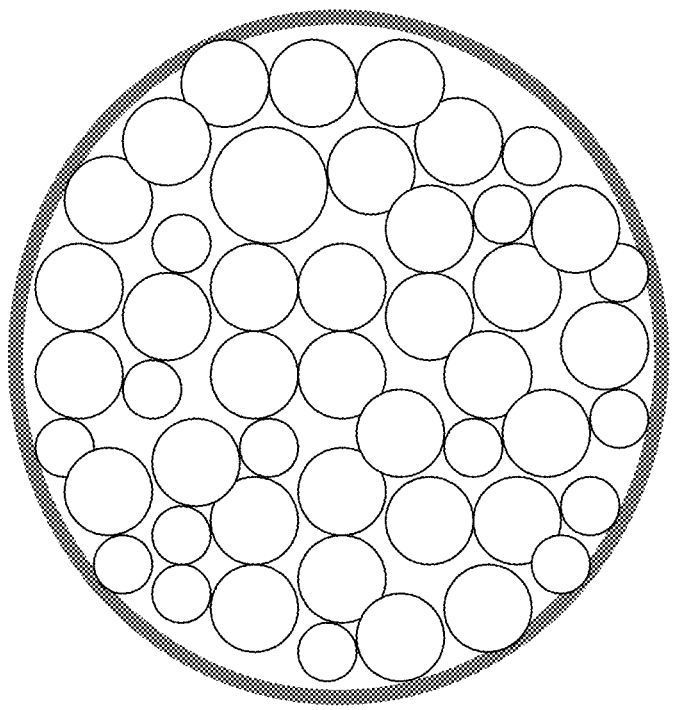
FIG. 6 is a schematic representation of a cross section of a scaffold of the invention.

The present invention comprises a composite scaffold composed of numerous bioactive glass fibers, that are optionally thermally or otherwise bonded together to form a core of longitudinally aligned oriented fibers, as described hereinabove. This core is encased in or surrounded by a biodegradable polymer layer which imparts superior mechanical properties compared to a similar scaffold composed of glass fibers alone. FIG. 4 depicts examples of the composites of the invention, as described further in below Example 2. The set of three composite scaffolds on the far left designated "Epoxy" are cores of bonded fibers wherein the bonded cores have been coated with an epoxy polymer. This can be accomplished by spraying, dipping, or painting, for example. The set of three composite scaffolds designated "Heat Shrink 1" comprise cores of fibers wherein the cores are bound together by a heat shrink polymer which has been wrapped around the core and then shrunk. FIG. 5 depicts a schematic cross-section of the epoxy-polymer coated embodiment where the pre-formed core is sprayed, painted, or dip-coated with an epoxy. FIG. 6 depicts a schematic cross-section of the version with a heat-shrink polymer film wrapped around the core. This is schematic only, as in the actual product the outer film is much more snug and tight around the core and in full contact with the outer surface of the core, as can be seen with the Heat Shrink 1 version shown in FIG. 4.

This composite scaffold with longitudinally co-aligned glass fibers is stronger than a scaffold composed of randomly oriented fibers when bending or tensile loads are applied to it since all of the individual fibers are aligned in the direction best able to withstand tensile stresses. Furthermore, the polymer layer encapsulating the core serves to reduce the bending/tensile stresses that are produced at the surface of the glass core since a portion of the load is carried by the polymer. In addition, the polymer layer serves to distribute any localized bending stresses created within the glass core which also reduces the likelihood of failure. Moreover, the polymer layer creates beneficial compressive stresses as it shrinks and squeezes the glass core. These forces help hold the glass fibers in place so that if one or more fibers do fail, the broken fibers are held in place by the polymer and the load is transferred to adjacent glass fibers. Also, there is a higher probability that a crack will stop before it propagates completely across multiple fibers in a core compared to when it must only propagate across a core composed of a single fiber or rod. A composite scaffold, therefore, composed of a bonded assembly of many individual fibers, rather than a single glass rod of the same size, and enclosed in a ductile polymer layer is not only stronger, but also less likely to fail catastrophically.

The polymer for the polymer film is selected from the group of polymers consisting of polycaprolactones (PCL), poly-L-Lactic acid (PL-LA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly(anhydrides), poly(hydroy acids), polyglycolides, polylactides, poly(propylene fumerates), polyacetals, polycarbonates, polyamino acids, poly)orthoesters), polyamides, poly(vinyl pryyolidones), poly(dioxanones), polyhydroxyvalyrates, polyhydroxybutyrates, biodegradable polycyanoacrylates, biodegradable polyurethanes, poly(methyl vinyl ether), poly(esteramides), polyketals, poly(glyconates), poly(maleic anhydride), poly (maleic acid), poly (alkylene succinates), poly(ppyrrole), polyphosphazines, poly(maleic anhydride), tyrosine-based polymers, polysaccharides, poly(alkylene oxalates), poly(orthocarbonates), poly(ethylene oxide), polyureas, poly(ethylene vinyl acetate), polystyrene, polypropylene, polymethacrylate, polyethylene, poly(aniline), poly(thiophene), non-biodegradable polyurethanes, co-polymers, adducts, and mixtures thereof. In one preferred embodiment the composite scaffolds are made using PCL and/or other biodegradable polymers such as polylactic acid (PLA) and various co-polymers.

The thickness of the polymer layer ranges, for example, from 250 to 1000 microns, such as about 500 microns. Accordingly, the polymer film has a thickness between about 5 microns and about 1000 microns, such as between about 200 and about 600 microns. An internal porosity greater than 25 vol % is considered desirable (for bone in-growth).

For the best strength characteristics for load-bearing applications, the above-described core composed of longitudinally aligned fibers will normally be preferred. However, in those applications were flexural strength is not a primary factor, for example, where the forces are small or negligible, a bonded, porous network of either glass particles and/or randomly oriented fibers encased in the biodegradable polymer film could be suitable. The glass particles, at least about 75% of the glass particles, have a particle size between about 40 and about 425 microns, for example between about 150 and about 355 microns. Or the longitudinally aligned fibers, randomly oriented fibers, and/or randomly oriented glass particles can alternatively be encased in a tube as discussed in connection with below Example 9, where the tube is either a biodegradable polymer such as those of the film discussed above, or where the tube is a biodegradable metal, such as certain magnesium alloys.

In a further alternative, the polymer layer does not encase the core in a continuous manner from one end to the other. From the standpoint of the stresses, the largest tensile stresses upon bending are at the mid-point of the glass core. Thus, in this alternative, the glass core is enclosed at the area of large tensile stress for a selected distance in each direction. Then there are alternating bare/enclosed sections along the rest of the scaffold until the end is reached.

In a further alternative, the core of glass fibers can be encapsulated with polymer fibers. Polymer fibers with a diameter ranging from 50 µm to 3000 µm with a circular, semi-circular, or rectangular (ribbon) cross section can be used. Or composite fibers of this geometry comprising a polymer which contains glass, ceramic or other solid materials in the form of particles, spheres, fibers, etc. can also be used to encapsulate the glass fiber core. These polymer or composite fibers are wrapped tightly around the scaffold core in a generally circumferential direction between about 90 degrees from the longitudinal axis of the core to about 75 degrees from the longitudinal axis in one or more layers wrapped in one or more direction. Compressive stresses are thereby applied to the core of bonded glass fibers so as to reduce the tensile stresses in the core when the scaffold is subjected to flexural loads. This alternative can be applied to cores with and without the above-described encasing polymer films.

The cores of the composites of the invention have excellent capillary flow characteristics. The velocity at which the liquid penetrates (moves upward through) the glass fiber core depends upon several factors such as the microstructure of the fiber core, the amount of porosity, the degree to which the pores are interconnected, the size and shape of the pores, and the viscosity of the liquid. The average velocity of fluid uptake for scaffolds of the invention in one set of tests ranged from 4.5 to 7.5±2 mm/s. In general, the velocity is expected to increase with an increase in porosity. The practical value of this velocity is that it is an indicator as to how quickly body fluids and cells can penetrate a scaffold (of fixed or varying geometry/microstructure) and become available to react with the bioactive glass fibers to commence the formation of new soft or hard (bone) tissue. This simple measurement shows that a liquid with a viscosity close to that of water or blood plasma penetrates very rapidly into a unidirectional scaffold composed of thermally-bonded bioactive glass fibers, with a porosity of 20 to 25%. For practical purposes, the penetration is instantaneous. This is a very desirable feature of such a scaffold. In practice, the surgeon would probably soak the scaffold in the patient's blood/body fluids/bone marrow/drugs for a few minutes so that the scaffold is saturated before it is placed in the patient's body.

The scaffold of the invention is suitable in one aspect for forming a complete replacement bone or tissue segment where the mammal's original bone has been removed, crushed, decimated by disease or the like. In another aspect the scaffold is suitable as a bridge such as between about 2 mm and about 25 mm in length for bridging two separated bone segments. The scaffold is intended to serve as a temporary bridge for facilitating fluidic (e.g., marrow) communication (or transport) between the separated bone segments, thereby facilitating the healing of the broken bones. The scaffold also serves as an internal splint providing support for the bone fracture while the bone heals.

The flexural strength of the rigid scaffold body is at least about 40 MPa, such as between about 40 and about 200 MPa, such as between about 75 and about 125 MPa. The flexural strength of the core is less than about 40 MPa, such as less than about 10 MPa. In certain embodiments, the flexural strength of the core is less than about 50%, such as less than about 10%, of the flexural strength of the scaffold body comprising the core and the polymer film.

The polymer film in certain embodiments encapsulates the scaffold body along some fraction of its length but not at its ends, so the scaffold body is open with its core exposed at selected locations along its length and at its ends. For most embodiments it is preferred that the fibers of the core are bonded together, for example are thermally fused together.

In one variation, the fiber core contains hollow glass fibers and solid glass fibers for porosity and penetration of body fluids into the scaffold. In another variation, the polymer film is selectively perforated or porous to allow body fluids to penetrate the glass fiber core. It is also optional that the fiber core comprises a mixture of biodegradable glass fibers of different chemical composition that degrade in-vivo at different rates, and which can release different chemical elements that are osteogenic or angiogenic or antimicrobial. Furthermore, the fiber core may comprise some elements that are radio-opaque (like bone) such that X-rays taken at periodic times can be used to judge bone healing process as radio-opacity of the core changes with time. Optionally, the polymeric film is a composite film which contains biodegradable glass particles, fibers, or spheres such that as the particles, fibers, or spheres react in-vivo there is an increase in the microporosity of the film to facilitate greater body fluid ingress. In a further variation, the core contains glass fibers whose cross section varies along the length of the fibers, being larger at certain locations than at other locations.

The following non-limiting examples further illustrate the invention.

EXAMPLE 1

Fibers of the bioactive glass type 13-93 (~2.4 grams) produced at Missouri University of Science & Technology having diameters in the range of about 50 to about 400 microns and lengths of about 62 mm were placed inside a graphite mold formed by hollowing out a graphite cylinder. The mold was then placed in a furnace (Neytech Model 2-525) and heated in air to a temperature of about 700° C., where it was held for times ranging from 5 to 45 minutes. The heat source was discontinued and the mold cooled to room temperature at an average cooling rate of about 30° C./min. Cylindrical scaffolds of unidirectional self-bonded fibers were removed from the mold, sectioned, and photographed to provide the images in FIGS. 1A, 1B, and 1C. The diameter of the scaffolds was 6 mm. FIG. 1A depicts a scaffold heated for a shorter period of time having a lower degree of self-bonding, higher porosity, and lower strength. FIGS. 1B and 1C depict a scaffold heated for a longer period of time, having a greater degree of self-bonding, lower porosity, and greater strength. In 1B and 1C the pore size is approaching too small, thereby inhibiting fluid flow in the scaffold in comparison to FIG. 1A. Open pores of at least about 100 microns in cross section are required for bone growth.

EXAMPLE 2

Figure 7:
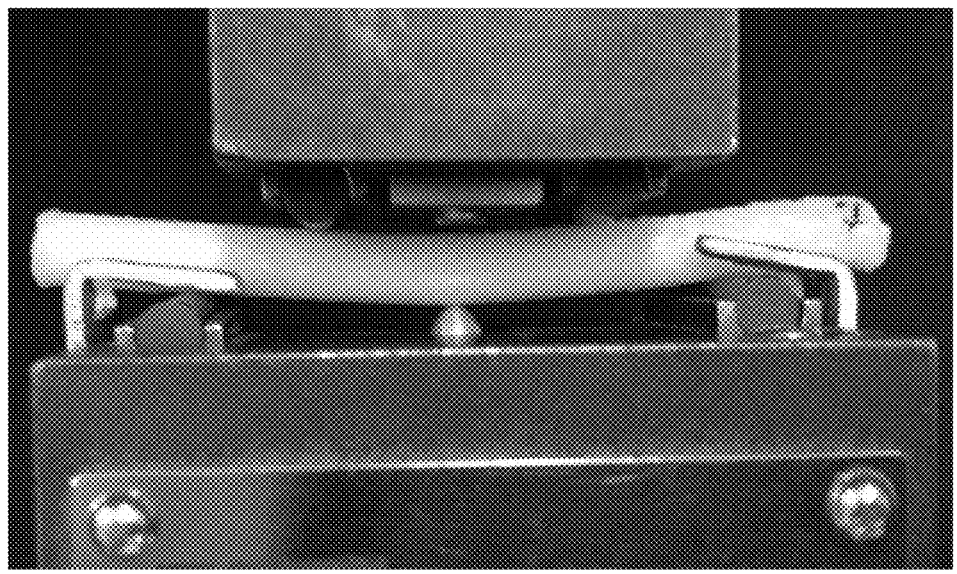
FIG. 7 is a photograph of a four-point bending test performed on a scaffold of the invention.

Composite scaffolds composed of a core of thermally-bonded, unidirectional fibers of a bioactive silicate glass encapsulated in a polymer layer were prepared and tested in four-point bending, and the results presented in FIG. 4. The cores were prepared in accordance with Example 1. The composite scaffolds were about 5 mm in diameter and about 50 mm in length, and were coated with an epoxy and two different heat shrink polymers. The samples were tested in four-point bending tests as shown in FIG. 7 with an outer span of 40 mm and inner span of 20 mm. The set of three composite scaffolds on the far left designated "Epoxy" are cores of bonded fibers wherein the bonded cores have been coated with an epoxy polymer. The set of three composite scaffolds designated "Heat Shrink 1" comprise cores of fibers wherein the cores are bound together by a heat shrink polymer which has been wrapped around the core and then shrunk. An additional "Heat Shrink 2" set of this type was prepared and tested as shown, though the scaffolds themselves are not shown in FIG. 4. FIG. 4 shows that the average flexural strength of the composite scaffolds was at least twice that of bare scaffolds. The bare scaffolds were the same type of thermally-bonded, co-aligned 1393 glass fiber cores used for the composite scaffolds, but without the outer polymer layer. These data for composite scaffolds demonstrate the beneficial effect of the polymer layer since the composite scaffolds are nearly twice as strong as the bare scaffolds. Three distinct bars are shown for each of the three sets Epoxy, Heat Shrink 1, and Heat Shrink 2; and the horizontal line connects the average flexural strength for the three samples tested in each group. The internal porosity of the composite scaffolds varied from 20% to 25%. Other tests show that composite scaffolds having a porosity of about 25% made with a biodegradable polymer, poly-caprolactone (PCL) film surrounding the foregoing glass fiber core, had an average flexural strength of 71 MPa. This compares very favorably with the strength of cortical bone which ranges from 50 to 150 MPa.

Figure 8:
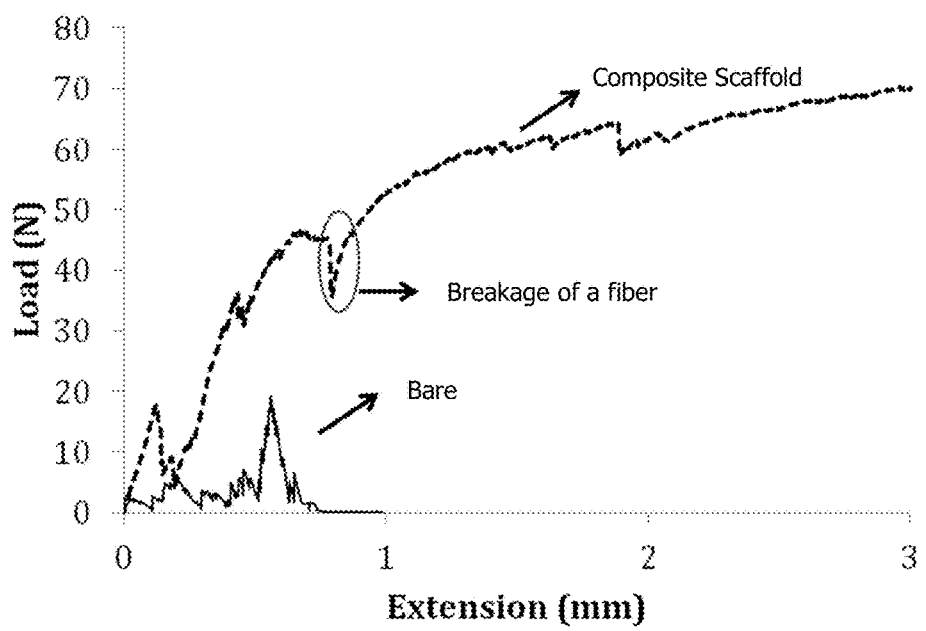
FIG. 8 is a graphical presentation of load versus deformation data for a composite scaffold of the invention in comparison to a scaffold of the type disclosed in U.S. Pat. No. 8,353,966.

Load versus deflection curves under four-point bending for a composite scaffold of the current invention comprising a heat shrink polymer and a glass fiber core in comparison to a bare scaffold of the same 1393 co-aligned glass fibers are shown in FIG. 8. The dashed line is for the composite scaffold with polymer film and the solid line is for the bare scaffold. The interruptions or discontinuities in the curve for the composite scaffold are attributed to the localized failure of individual glass fibers. The composite scaffold is not only much stronger than the bare scaffold, but it also continues to be load bearing even after some fraction of the glass fibers have broken. This shows that in addition to a higher flexural strength, the composite scaffold fails under load in a way different from that of a bare scaffold, which simply fails catastrophically as is typical for a brittle glass. The composite scaffold undergoes much greater deflection without physical failure as shown in FIG. 7, wherein the composite scaffold is under load. Even though some portion of the glass fibers are believed to have failed, the composite scaffold remains in-tact and capable of bearing a significant load. This ductile behavior is highly desired and is a major improvement in performance compared to a bare fiber scaffold which fails catastrophically.

As a general proposition, the composite scaffolds of the invention have suitable strength on account of the bare co-aligned glass fiber core and the polymer casing, which in one embodiment as described is a wrapped polymer film, and in other embodiments is applied by fluid methods such as spray, paint, or dip.

The following Examples 3 through 8 are taken from co-assigned U.S. application Ser. No. 13/740,365, published as 2013/0144400, and describe certain features of the scaffolds of that application and U.S. Pat. No. 8,353,966. These scaffolds are suitable scaffold cores for use in the currently claimed invention. Examples 9-12 are taken from the same application, and describe additional scaffolds that are described and claimed in the prior applications. These scaffolds are also suitable scaffold cores for use in the currently claimed invention. As a general proposition, however, these scaffolds employ reinforcing mechanisms which are not necessary in scaffold cores in the context of the present invention, which instead employ an external polymer film for reinforcing. However, the present invention does not preclude and affirmatively encompasses scaffold cores which approximate the scaffolds shown in Examples 9-12.

EXAMPLE 3

Figure 9A:
FIGS. 9A and 9B are photographs of a segment of scaffold core of the invention after immersion in an osteoblast cell culture and MTT labeling.
Figure 9B:
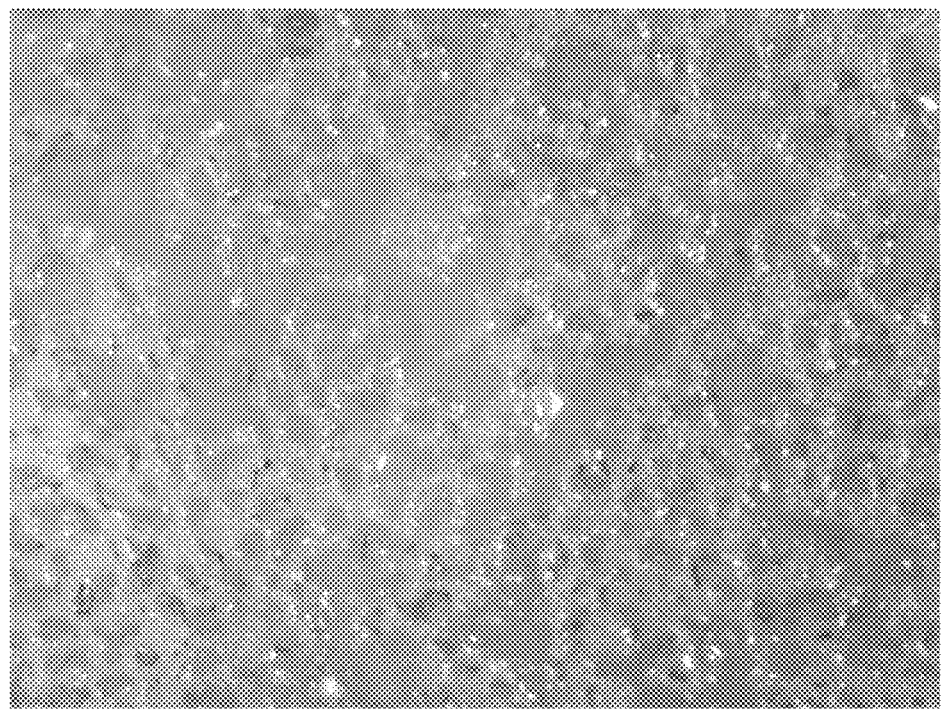

A 6 mm diameter by 20 mm thick section of a unidirectional scaffold core produced according to Example 1 was placed in a culture of osteoblast cells for four hours. MTT labeling was then performed on the section and photographs were taken (FIGS. 9A and 9B). The dark spots are due to the uptake of viable osteoblast-like cells into the scaffold.

EXAMPLE 4

Figure 10:
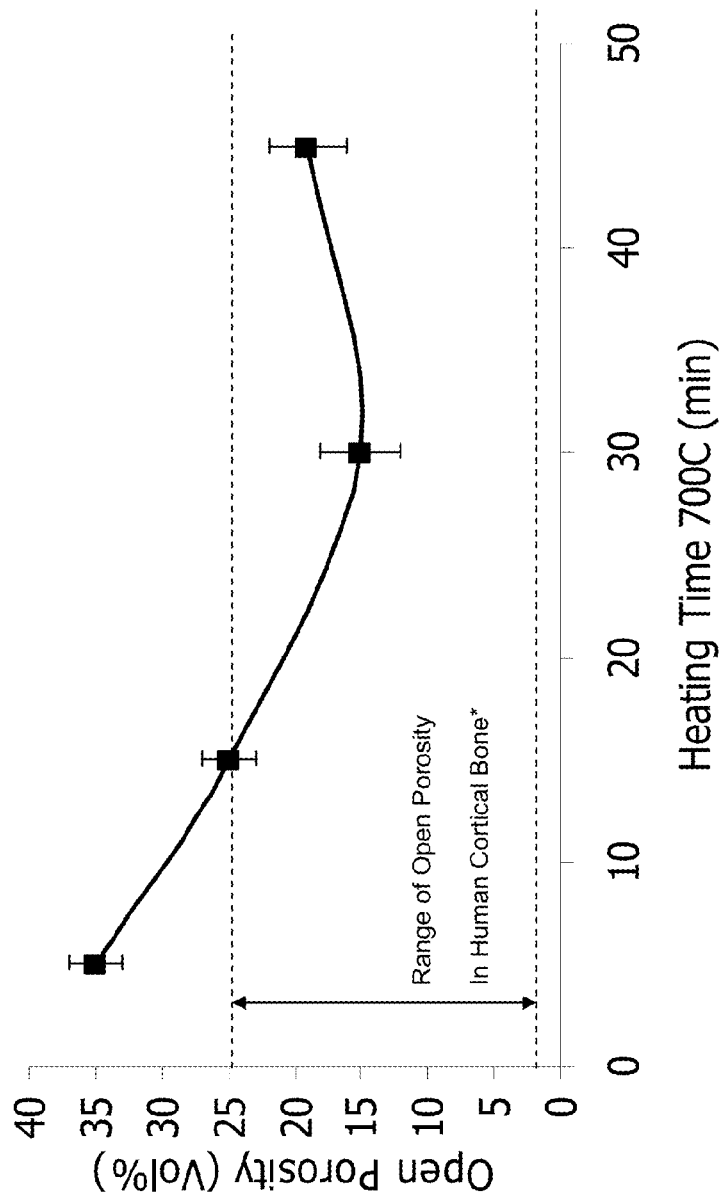
FIG. 10 is a graphical plot of open porosity data of scaffold cores of the invention.

Undirectional glass scaffolds were prepared in accordance with Example 1 with joining/heating times at 700° C. of 5, 15, 30, and 45 minutes. The open porosity of each scaffold was then determined by the Archimedes liquid displacement method to be 35, 25, 15, and 18 vol %, respectively; see FIG. 10. This degree of open porosity is within the range of human cortical bone and was achieved for scaffolds heated for 15, 30, and 45 minutes.

EXAMPLE 5

Figure 11:
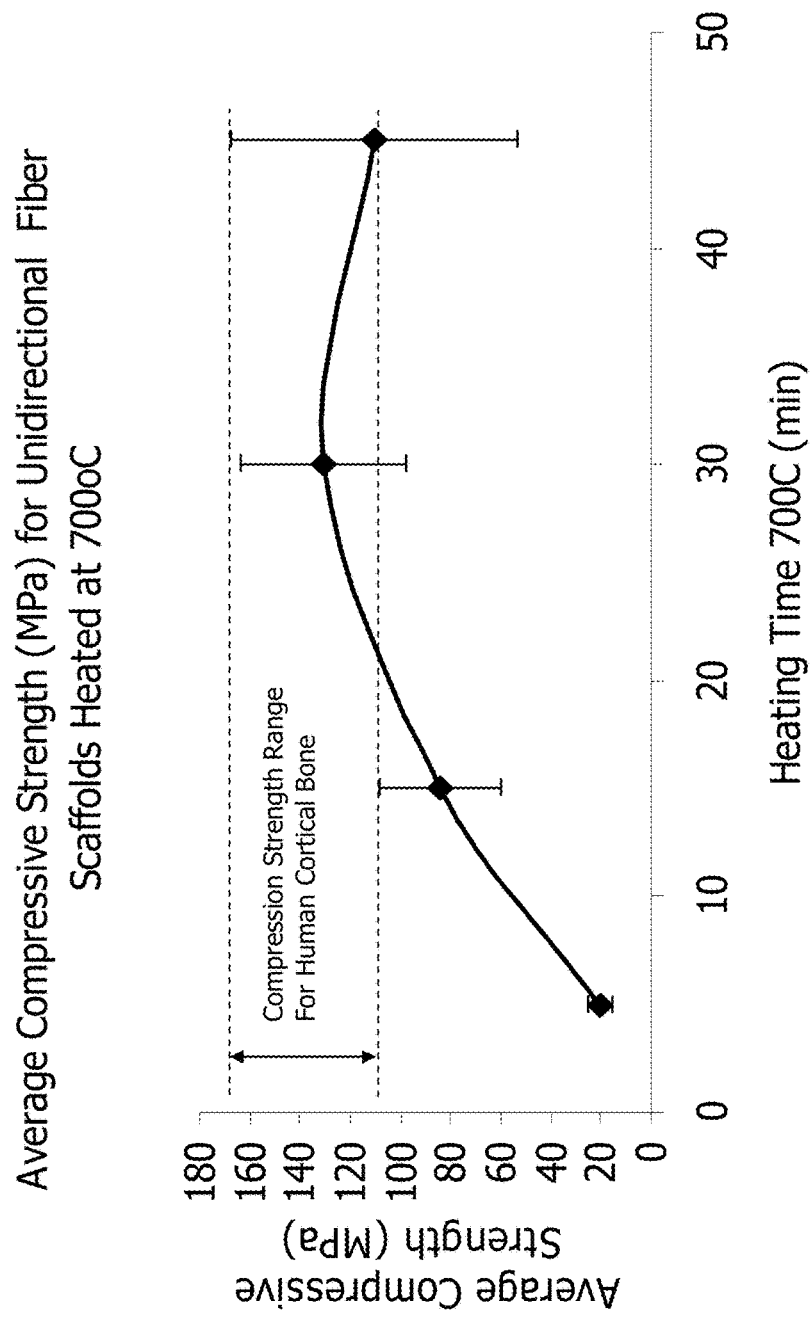
FIG. 11 is a graphical plot of compressive strength data of scaffold cores of the invention.

Unidirectional glass scaffolds were prepared in accordance with Example 1 with joining/heating times at 700° C. of 5, 15, 30, and 45 minutes. The average compressive strength of each scaffold was then determined by mechanical compression testing (Instron mechanical test instrument Model 4204 with a crosshead speed of 0.5 mm/min) to be 20, 80, 130, and 112 MPa, respectively, see FIG. 11. This demonstrates that compressive strengths within the range of human cortical bone were achieved for the scaffolds heated for 30 and 45 minutes.

EXAMPLE 6

Figure 12A:
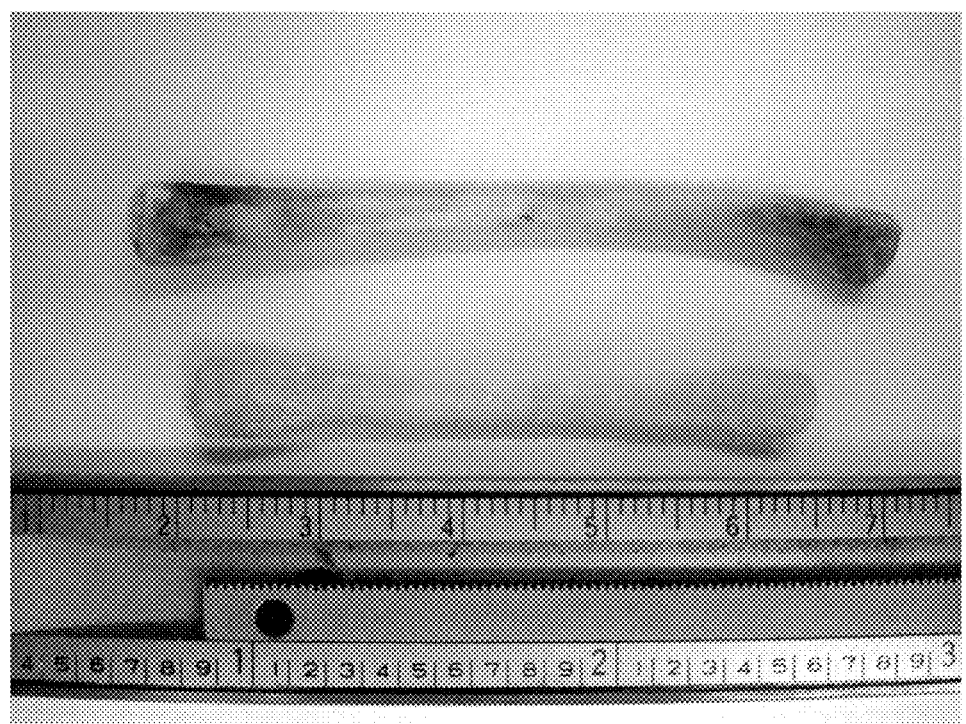
FIGS. 12A and 12B are photographs of a scaffold core of the invention next to a chicken bone.
Figure 12B:
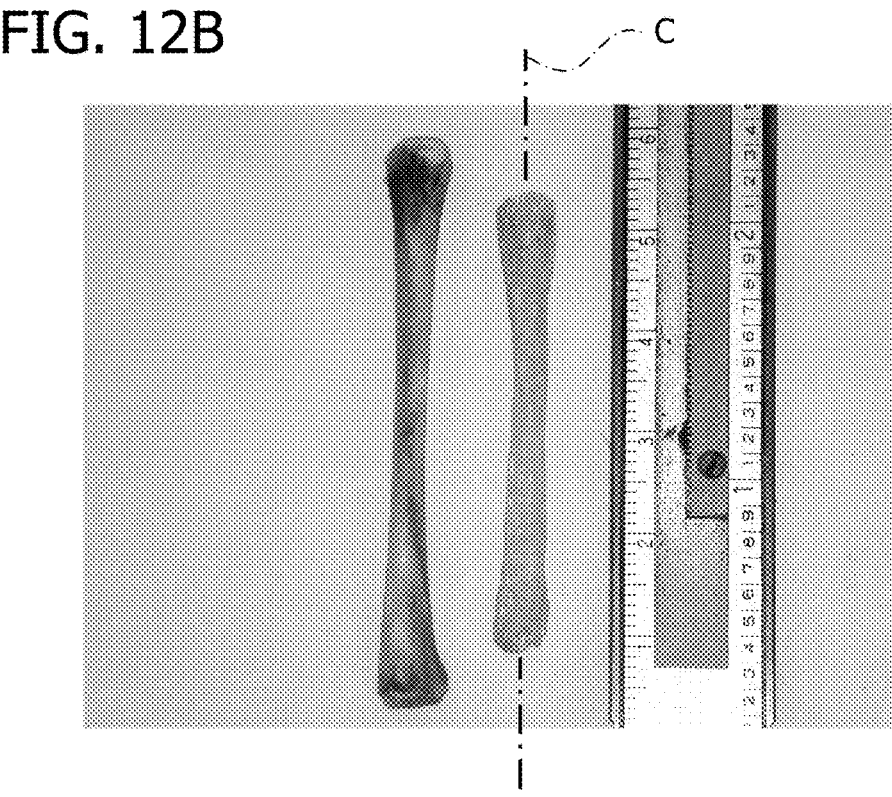
Figure 13A:
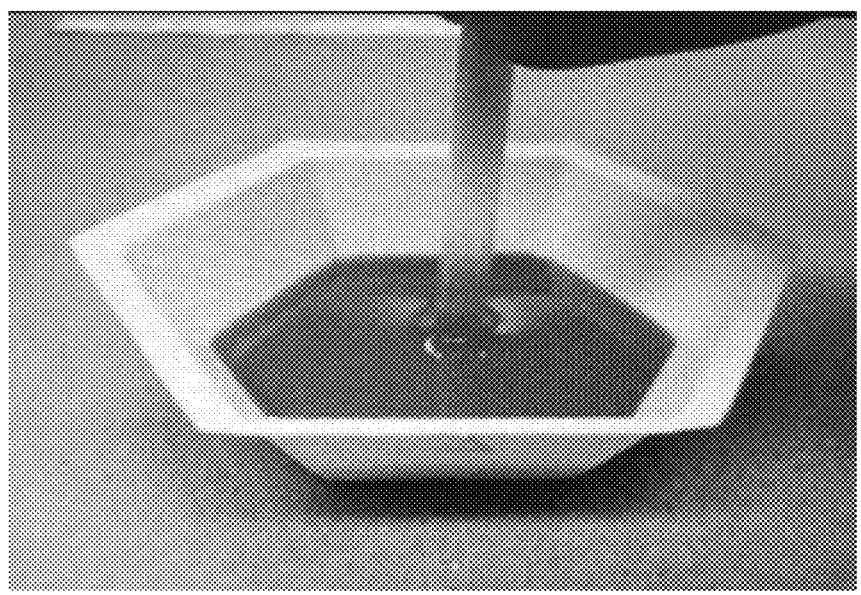
FIGS. 13A, 13B, 13C, and 13D are still frames extracted from videos taken of experiments described in the working examples.
Figure 13B:
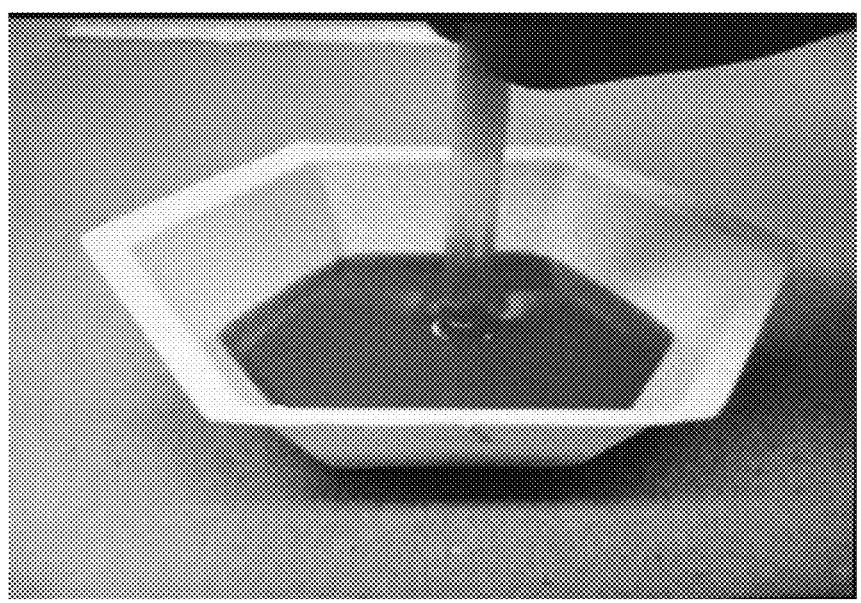
Figure 13C:
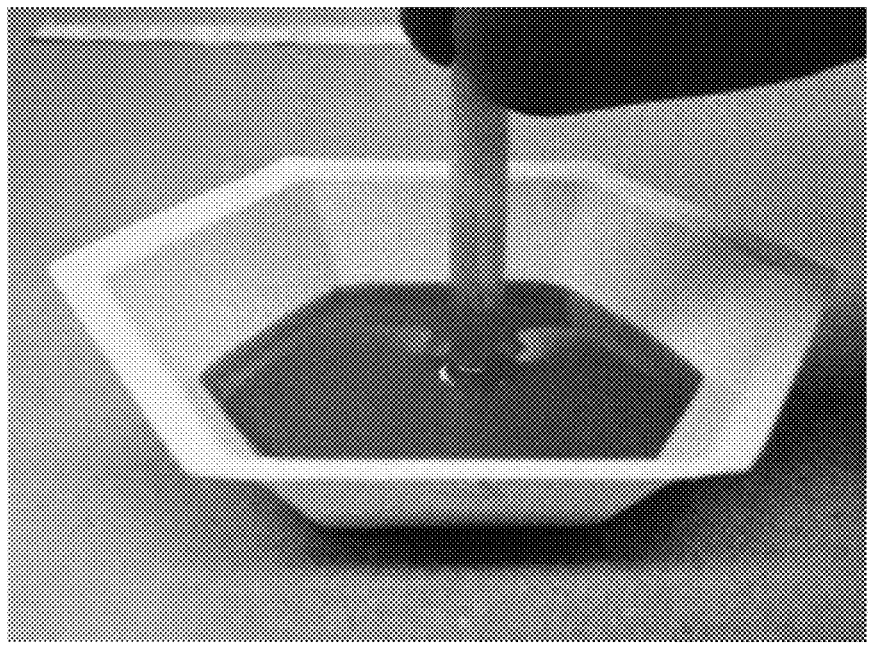
Figure 13D:
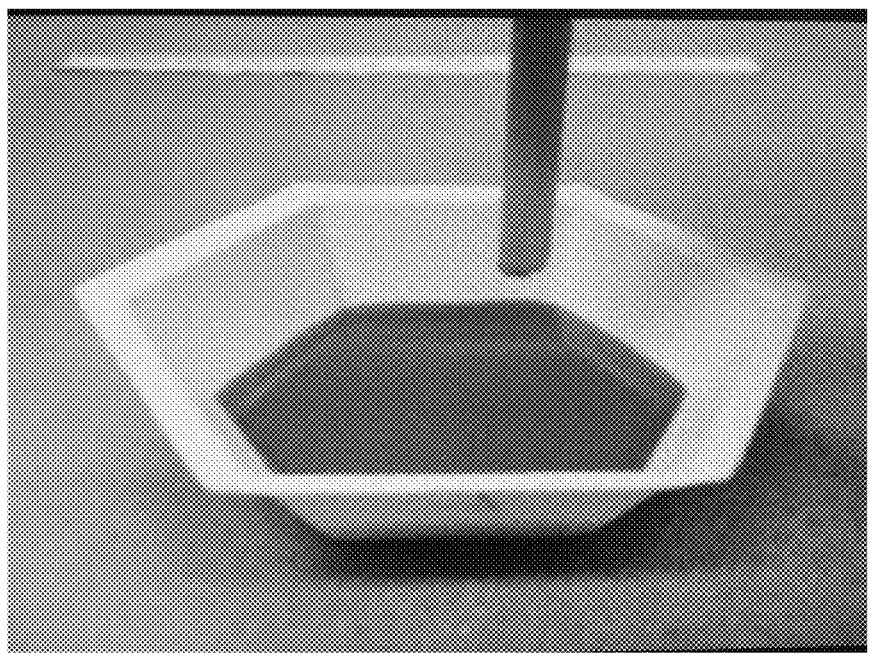

A unidirectional scaffold was prepared in accordance with this invention by molding, bonding, cooling, and then machining to mimic the configuration of a chicken bone. FIGS. 12A and 12B show the scaffold next to leg bone of a chicken. The scaffold of the invention, which is the lighter-colored of the two specimens closer to the ruler in FIG. 12, has a length of about 50 mm. This unidirectional scaffold is composed of fibers which were oriented parallel to the longitudinal axis of this object.

EXAMPLE 7

A unidirectional cylindrical glass scaffold was prepared in accordance with Example 1 having a length of about 62 mm and a diameter of about 6 mm. The fibers were type 13-93 bioactive glass having a length of about 62 mm and diameters ranging from about 50 to about 400 microns. The fibers were oriented parallel to the longitudinal axis of the scaffold. The tip of the scaffold was dipped in a glycerol solution (34 wt % glycerol-66 wt % distilled water) as shown in FIGS. 13A-13D. This solution has a viscosity of 2.5 centipoises at 25° C., which is in the average range for human blood. The purpose of this experiment was to demonstrate the strong capillary forces which this scaffold exerts upon a liquid resembling human blood.

A roughly 40 second video of the experiment was filmed, and frames at 9, 11, 15, and 22 seconds are shown in FIGS. 13A-13D, respectively. These frames show progressively upward darkening of the scaffold, which demonstrates rapid capillary uptake of the solution and its components into the scaffold, and that the scaffold of the invention has strong capillary uptake of fluid in the direction of the longitudinal axis of the fiber scaffold.

EXAMPLE 8

A cylindrical, unidirectional glass scaffold was prepared in accordance with Example 1 having a length of about 62 mm and a diameter of about 6 mm. The fibers were type 13-93 bioactive glass fibers having a length of about 62 mm and a diameter of about 50 to 400 microns. The fibers were oriented parallel to the longitudinal axis of the scaffold.

Figure 14A:
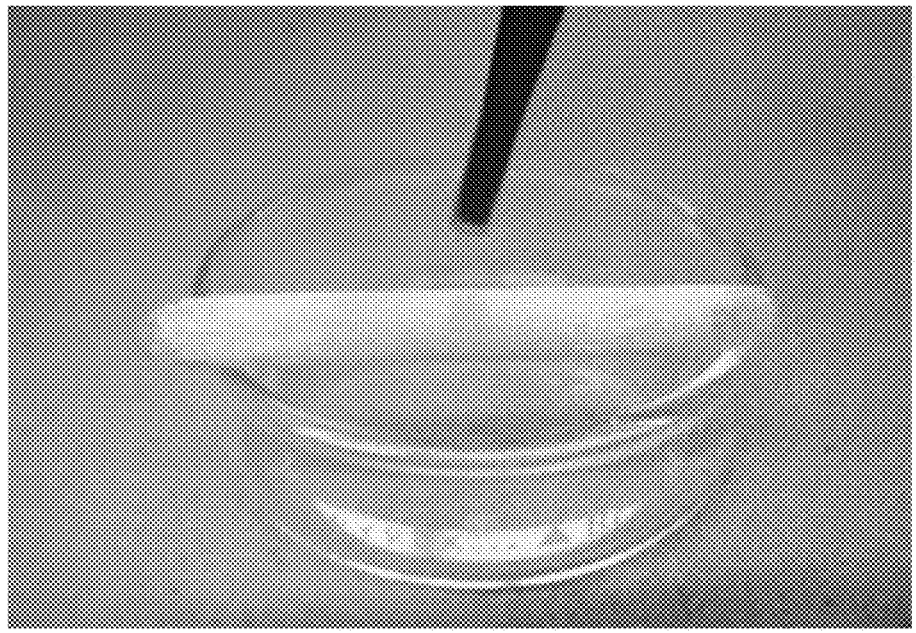
FIGS. 14A, 14B, 14C, and 14D are still frames extracted from videos taken of experiments described in the working examples.
Figure 14B:
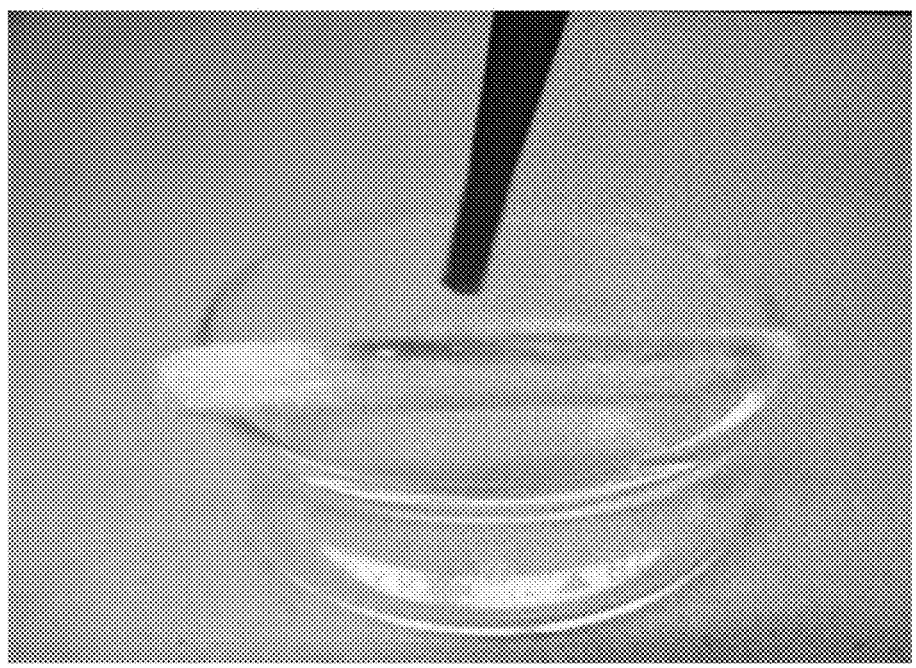
Figure 14C:
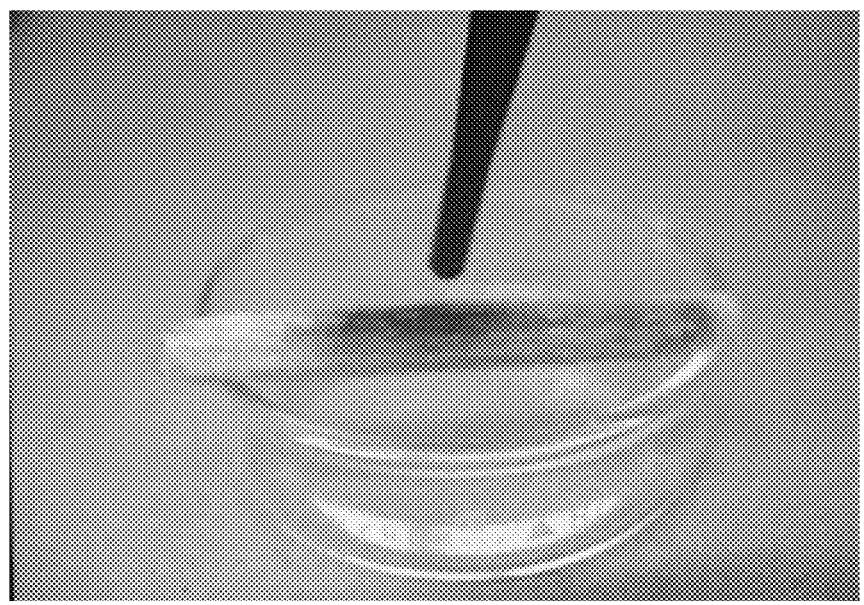
Figure 14D:
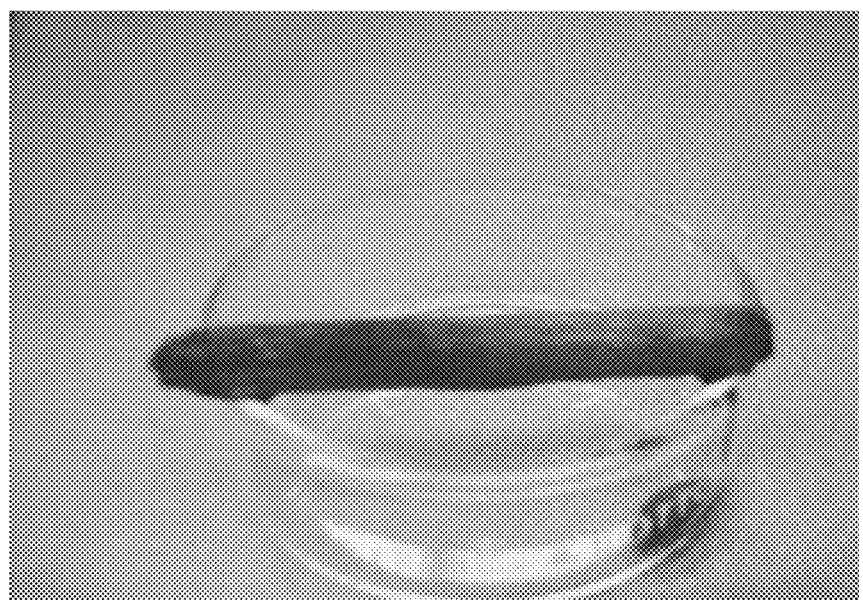

An eyedropper was used to drop the same water-glycerol solution as described in Example 7 onto the external surface of the scaffold as shown in FIG. 14A for the purpose of demonstrating the rapid capillary action of the scaffold in a direction perpendicular to the longitudinal axis of the scaffold. The solution was dropped fairly quickly drop-by-drop onto the external surface of the scaffold until the scaffold became saturated with the solution. A video of this experiment was made over a 50 second period. Frames at 4 seconds (0 drops), 12 seconds (3 drops), 18 seconds (6 drops), and 43 seconds (19 drops) are shown in FIGS. 14A, 14B, 14C, and 14D, respectively. These frames show rapid capillary uptake of the solution and its components into the scaffold in both the lengthwise and transverse directions. This experiment demonstrates the scaffold's high affinity for the liquid and that the scaffold retained most of the drops before becoming saturated. At the conclusion of this experiment most of the liquid was retained in the scaffold and very little of the solution had dripped out of the scaffold into the bowl, as shown in 14D.

EXAMPLE 9

Figure 15:
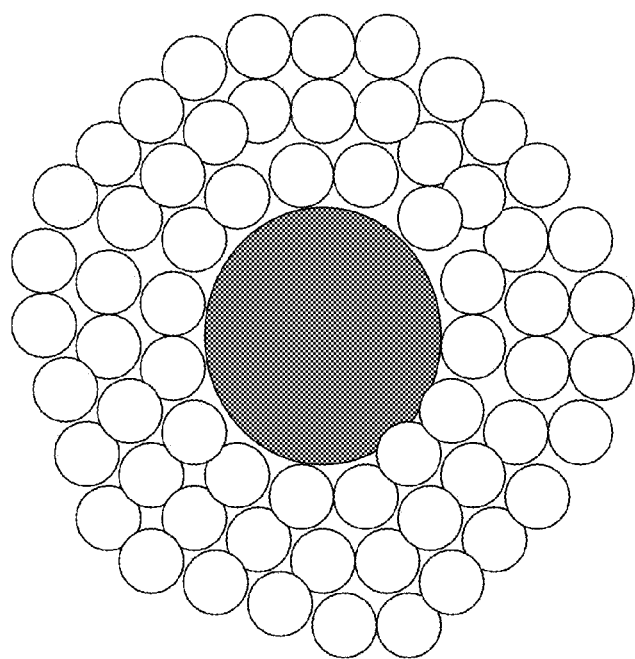
FIGS. 15, 17, 18, 19, 21, 23, 24, and 26 are schematic depictions of alternative reinforced scaffold core embodiments of the invention.
Figure 16:
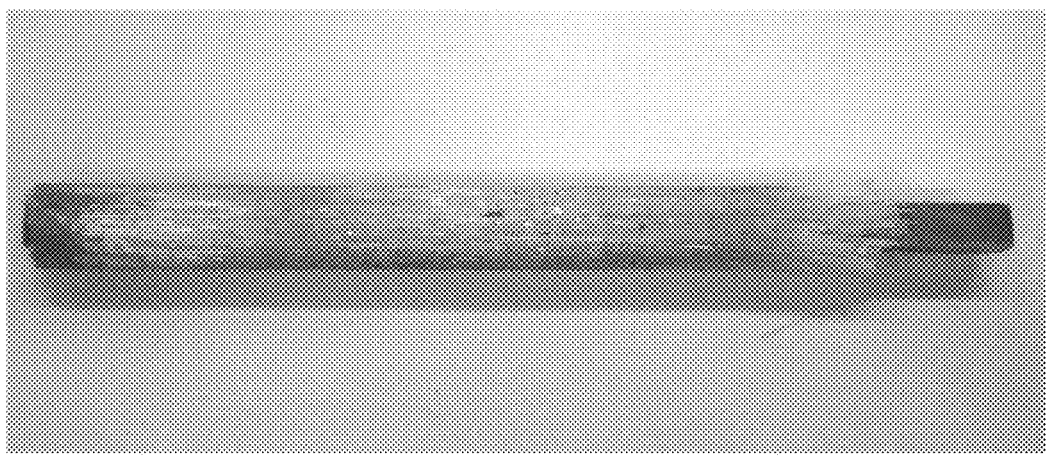
FIG. 16 is a photograph of a scaffold core of the schematic of FIG. 15.

In one alternative embodiment of the invention, a titanium or other biocompatible support such as a rod is incorporated into the scaffold to provide additional mechanical strength. A unidirectional scaffold was prepared generally in accordance with Example 1 having a length of about 62 mm and a diameter of about 6 mm. The fibers were type 13-93 bioactive glass fibers having a length of about 62 mm and a diameter of about 50 to 400 microns. The fibers were oriented in longitudinal co-alignment defining the length of the scaffold with an added reinforcing rod placed at the center of the fibers prior to self-bonding. FIG. 15 is a schematic pictorial demonstrating this concept of placing a reinforcement of Ti or other metal or alloy or supporting material in the center of a self-bonded unidirectional bioactive glass fiber scaffold. FIG. 16 is a photograph of the reinforced unidirectional bioactive glass scaffold prepared with a Ti rod placed in the center of a bundle of fibers, and heated so that the fibers self-bonded and also attached to the rod, in accordance with this example.

Figure 17:
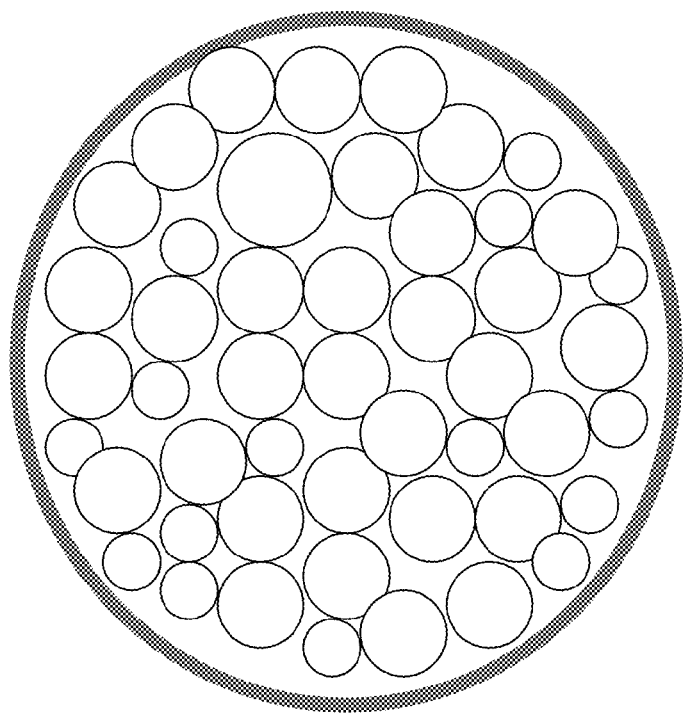

FIG. 17 is a schematic pictorial demonstrating an alternative concept of filling a hollow reinforcing tube of Ti or other metal or alloy or polymer including biodegradable polymers such as PCL or PLA or other supporting material with unidirectional glass fiber followed by self-bonding to form the scaffold. The tube is, for example, made of titanium or any other reinforcing material with similar thermal expansion properties of the glass so the scaffold bonds to the tube as the fibers self-bond. This may be beneficial in promoting bone ingrowth in prosthesis such as hip implants by inserting glass fibers into and around the implant as a means for improved bone attachment and ingrowth.

Figure 18:
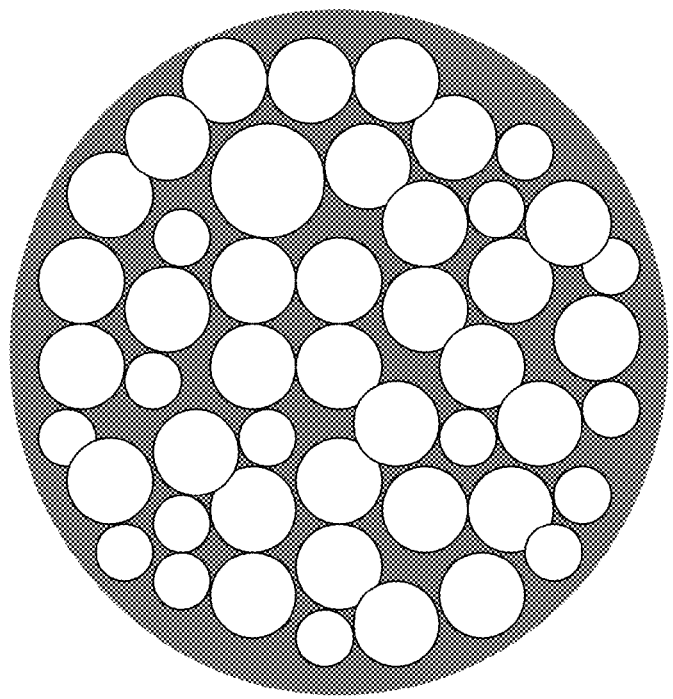

FIG. 18 is a schematic pictorial demonstrating a further alternative concept of a unidirectional bioactive glass scaffold filled with a polymer phase. Suitable polymers include those such as bone cement (PMMA) or biodegradable polymers such as PCL or PLA, as the polymer phase is used for sustained reinforcement (PMMA) or an initial reinforcement followed by a slow degradation of biodegradable polymer allowing new tissue to fill in with time. These methods associated with the foregoing can be practiced individually or in any combination for constructing or implementing a reinforced unidirectional bioactive glass scaffold.

EXAMPLE 10

Figure 19:
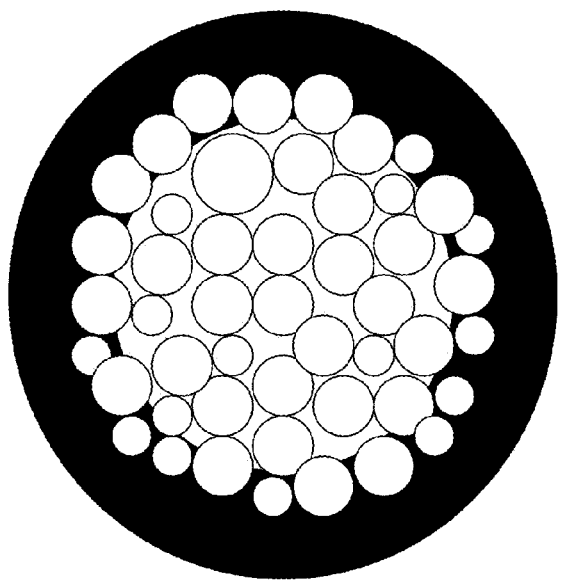
Figure 20:
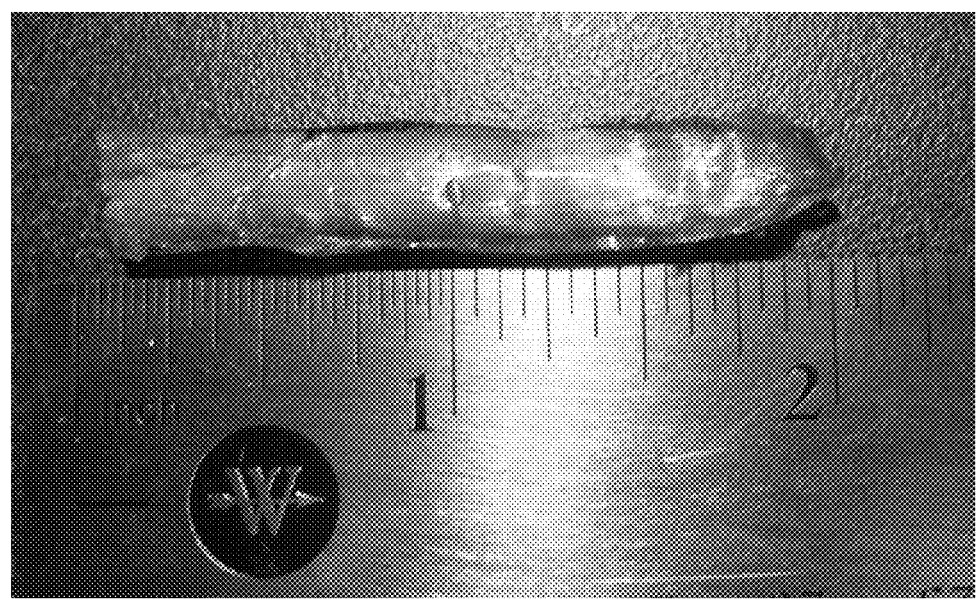
FIG. 20 is a photograph of a scaffold core of the schematic of FIG. 19.

FIG. 19 is a schematic illustration of an alternative embodiment of the invention in which biocompatible glass fibers longitudinally aligned in accordance with the invention are bonded together by dipping into a molten polymer to form a rigid outer layer, depicted as black in the figure. FIG. 20 is a photograph of a scaffold prepared this way by dipping a bundle of type 13-93 fibers into molten polymer of 82 parts polylactic acid (PLA) and 18 parts polyglycolic acid (PGA) at 250° C. The degradation rate can be controlled by selecting a mix of biocompatible polymers in proportions to impart the desired degradation. In this embodiment and other embodiments, it is also possible to spray or otherwise coat the individual fibers with a polymer such as PLA or PGA which affects degradation.

EXAMPLE 11

Figure 21:
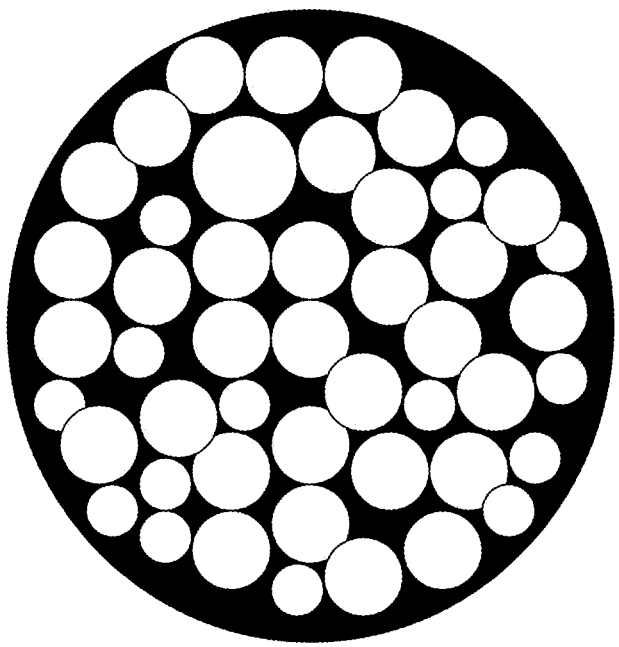
Figure 22:
FIG. 22 is a photograph of a scaffold core of the schematic of FIG. 21.

FIG. 21 is a schematic illustration of an alternative embodiment of the invention in which biocompatible glass fibers longitudinally aligned in accordance with the invention are bonded together by dipping into a bath of a polymer dissolved in a solvent. By dissolving the polymer in a solvent, the polymer depicted here in black is able to flow into the interior of the bundle of fibers, in contrast to the embodiment in FIG. 19. FIG. 22 is a photograph of a scaffold prepared this way by dipping a bundle of type 13-93 fibers into a polymer of 82 parts polylactic acid (PLA) and 18 parts polyglycolic acid (PGA) dissolved in a solvent.

EXAMPLE 12

Figure 23:
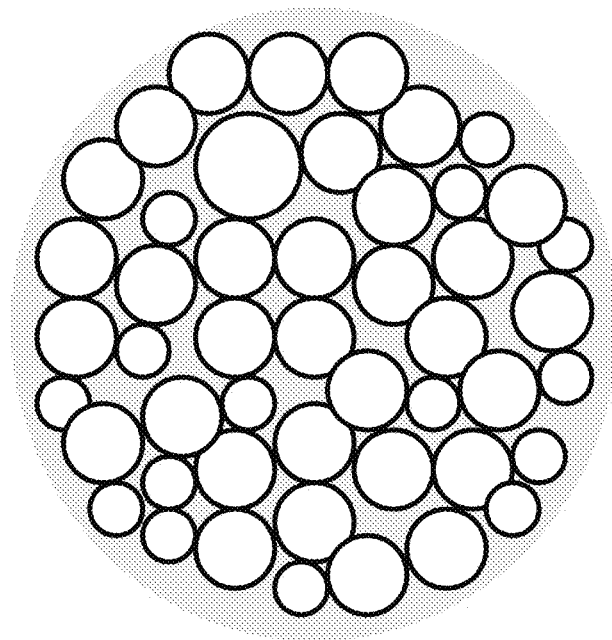
Figure 24:
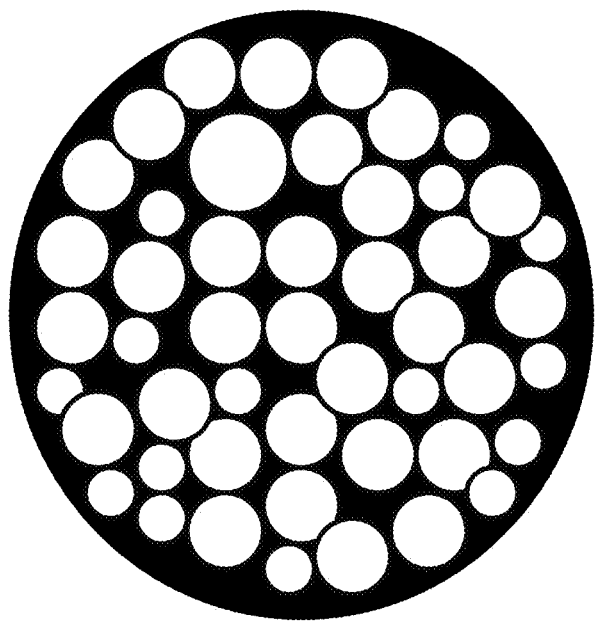
Figure 25:
FIG. 25 is a photograph of a scaffold core of the schematic of FIG. 24.

FIG. 23 is a schematic illustration of a further alternative embodiment of the invention in which biocompatible glass fibers longitudinally aligned in accordance with the invention are precoated with PLA, which are then bonded together as shown in FIG. 24. FIG. 25 is a photograph of a scaffold prepared this way by dipping a bundle of type 13-93 fibers into an 82:18 mixture of PLA/PGA in a solvent. In this embodiment, the thickness of the polymer coating is, for example, at least about 500 nm, such as between about 0.5 micron and about 10 microns, or between about 1 micron and about 5 microns.

Figure 26:
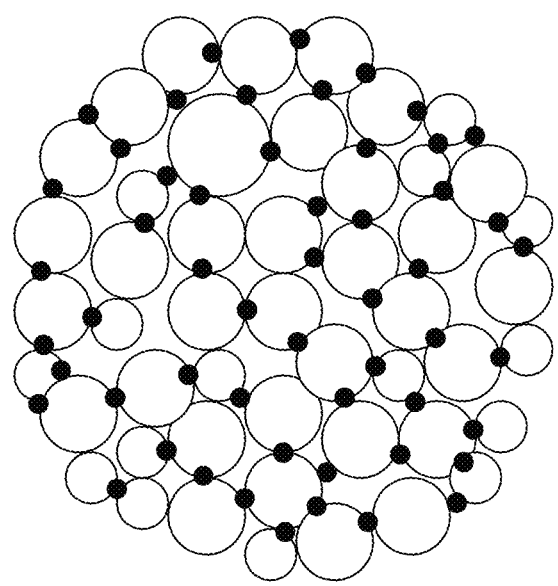

It can be seen from the above, therefore, that the rigidity required in the invention can be imparted by bonding the longitudinally aligned fibers to each other by polymer bonding. As further alternatives, the precoated longitudinally aligned fibers shown in FIG. 23 can be bonded to each other by exposing the polymer coating to a solvent to partially dissolve the coating. Then adjacent fibers bond to each other as the polymer re-solidifies upon removal of the solvent. Or the polymer coating on the fibers can be softened by heating, then hardened by cooling, leaving adjacent fibers bonded to each other. A still further alternative is to dust the fibers with polymer such that the polymer is more occasional and intermittent as shown in FIG. 26, in contrast to the continuous polymer coating shown in FIG. 23. Then the scaffold can be heated to soften the polymer such that it will bond the adjacent longitudinally aligned fibers at various points.

Among the polymer materials suitable for the various polymers described above are, for example, polycaprolactones (PCL), poly-L-Lactic acid (PL-LA), polyvinyl alcohol (PVA), polyglycolic acid (PGA), polyacrylic acids (PAA), poly ethylene glycol (PEG), poly-L-Lactic gylcolic acid (PLGA), polyesters, polyalkenoics, polyolefins, polysulfones, poly(anhydrides), poly(hydroy acids), polyglycolides, polylactides, poly(propylene fumerates), polyacetals, polycarbonates, polyamino acids, poly(orthoesters), polyamides, poly(vinyl pryyolidones), poly(dioxanones), polyhydroxyvalyrates, polyhydroxybutyrates, biodegradable polycyanoacrylates, biodegradable polyurethanes, poly (methyl vinyl ether), poly(esteramides), polyketals, poly (glyconates), poly(maleic anhydride), poly (maleic acid), poly (alkylene succinates), poly(ppyrrole), polyphosphazines, poly(maleic anhydride), tyrosine-based polymers, polysaccharides, poly(alkylene oxalates), poly(orthocarbonates), poly(ethylene oxide), polyureas, poly(ethylene vinyl acetate), polystyrene, polypropylene, polymethacrylate, polyethylene, poly(aniline), poly(thiophene), non-biodegradable polyurethanes, co-polymers, adducts, and mixtures thereof.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A tissue scaffold for repair and regeneration of bone hard tissue or muscle, skin, or organ soft tissue, including load-bearing bone tissue, the scaffold comprising:
    a core consisting of biocompatible, biodegradable inorganic glass fibers; and
    only a biocompatible, biodegradable, flexible polymer film surrounding the core and adhered to the core;
    wherein the core with surrounding polymer film is characterized by a flexural strength of at least about 40 MPa; and
    wherein the core is characterized by open and interconnected porosity to facilitate fluid flow into and lengthwise within the scaffold.

2. The scaffold of claim 1 wherein the polymer film has a thickness between about 5 microns and about 1000 microns.

3. The scaffold of claim 1 wherein the polymer film encapsulates the scaffold body along some fraction of its length but not at its ends, so the scaffold body is open with its core exposed at its ends.

4. The scaffold of the claim 1 wherein the core has a flexural strength of less than about 40 MPa.

5. The scaffold of the claim 1 wherein the core has a flexural strength of less than about 10 MPa.

6. The scaffold of the claim 1 wherein the core has a flexural strength which is less than about 50% of the flexural strength of the scaffold comprising the core and the polymer film.

7. The scaffold of claim 1 wherein the core has a flexural strength which is less than about 10% of the flexural strength of the scaffold comprising the core and the polymer film.

8. The scaffold of claim 1 wherein the fibers of the core are bonded together.

9. The scaffold of claim 1 wherein the fibers of the core are thermally fused together.

10. The scaffold of claim 1 wherein at least about 75 vol % of the fibers are longitudinally co-aligned and lie generally lengthwise along the scaffold central axis, are generally free of helical orientation about the scaffold central axis, and are arranged to define open channels within the scaffold which allow fluid flow into and lengthwise within the scaffold.

11. The scaffold of claim 1 wherein the fibers of the core consist of hollow glass fibers and solid glass fibers for porosity and penetration of body fluids into the scaffold.

12. The scaffold of claim 1 wherein the polymer film is selectively perforated or porous to allow body fluids to penetrate.

13. The scaffold of claim 1 wherein the fibers of the core consist of a mixture of biodegradable glass fibers of different chemical composition that degrade in-vivo at different rates, and which can release different chemical elements that are osteogenic or angiogenic or antimicrobial.

14. The scaffold of claim 1 wherein the polymeric film is a composite film having a microporosity and which contains biodegradable glass particles, fibers, or spheres such that as the particles, fibers, or spheres react in-vivo there is an increase in the microporosity of the film to facilitate greater body fluid ingress.

15. The scaffold of claim 1 wherein the core fibers consist of glass fibers with a cross section that varies along a length of the fibers, being larger at certain locations than at other locations.

16. The scaffold of claim 1 wherein:
    the polymer film has a thickness between about 5 microns and about 1000 microns;
    the polymer film encapsulates the scaffold body along some fraction of its length but not at its ends, so the scaffold body is open with its core exposed at locations along its length and at its ends;
    the core has a flexural strength of less than about 40 MPa;
    the flexural strength of the core is less than about 50% of the flexural strength of the composite scaffold comprising the core and the polymer film;
    the fibers of the core are bonded together.

17. The scaffold of claim 1 wherein:
    the polymer film has a thickness between about 5 microns and about 1000 microns;
    the polymer film encapsulates the scaffold body along some fraction of its length but not at its ends, so the scaffold body is open with its core exposed at locations along its length and at its ends;
    the core has a flexural strength less than about 40 MPa;
    the flexural strength of the core is less than about 10% of the flexural strength of the composite scaffold comprising the core and the polymer film;
    the fibers of the core are bonded together.

18. The scaffold of claim 1 wherein the polymer film is wrapped around the core and adhered to the core.

19. The scaffold of claim 18 wherein the fibers of the core are thermally fused together.

20. The scaffold of claim 1 wherein the polymer film comprises a ductile polymer.

21. The scaffold of claim 1 wherein the interconnected porosity is from about 10 vol % to about 35 vol %.

22. The scaffold of claim 1 consisting of:
    the core, wherein the core consists of biocompatible, biodegradable inorganic glass fibers; and
    the biocompatible, biodegradable, flexible polymer film surrounding the core and adhered to the core.

23. The scaffold of claim 1 wherein the fibers of the core are longitudinally co-aligned.

24. The scaffold of claim 1 wherein the fibers of the core have a diameter between about 20 microns and about 5,000 microns.

25. The scaffold of claim 1 wherein the fibers of the core have a length between about 6 mm and about 15 cm.

26. The scaffold of claim 1 wherein the fibers of the core have a length which is at least about 10 times the diameter of the fibers of the core.

27. The scaffold of claim 1 wherein at least about 85 vol % of the fibers of the core extend the entire length of the scaffold.

28. The scaffold of claim 1 wherein the core consists of glass fibers having a diameter between 100 and 450 microns.

29. The scaffold of claim 1 wherein the polymer film has a thickness between 200 and 600 microns.

30. The scaffold of claim 1 wherein the polymer film is adhered to the core by wrapping the film around the core followed by heating, or by spraying liquid polymer on the core, by painting of the film on the core, or by dipping the core into liquid polymer followed by hardening.

31. A tissue scaffold for repair and regeneration of bone hard tissue or muscle, skin, or organ soft tissue, including load-bearing bone tissue, the scaffold comprising:
    a core consisting of biocompatible, biodegradable inorganic components selected from the group consisting of longitudinally aligned fibers, randomly oriented fibers, and randomly oriented glass particles; and only a biocompatible, biodegradable, flexible polymer film surrounding the core and adhered to the core;

wherein the core with the surrounding polymer film is characterized by a flexural strength of at least about 40 MPa; and wherein the core is characterized by open and interconnected porosity to facilitate fluid flow into and lengthwise within the scaffold.

32. A tissue scaffold for repair and regeneration of bone hard tissue or muscle, skin, or organ soft tissue, including load-bearing bone tissue, the scaffold consisting of:

a core consisting of biocompatible, biodegradable inorganic glass fibers or consisting of biocompatible, biodegradable inorganic components selected from the group consisting of longitudinally aligned fibers, randomly oriented fibers, and randomly oriented glass particles; and a biocompatible, biodegradable, flexible polymer film having a thickness between about 200 and about 600 microns surrounding the core and adhered to the core;

wherein the core with surrounding polymer film is characterized by a flexural strength of at least about 40 MPa; and wherein the core is characterized by open and interconnected porosity to facilitate fluid flow into and lengthwise within the scaffold.

* * * * *